United States Patent [19]
Yoon

[11] Patent Number: 5,908,429
[45] Date of Patent: Jun. 1, 1999

[54] METHODS OF ANATOMICAL TISSUE LIGATION

[76] Inventor: InBae Yoon, 2101 Highland Ridge Dr., Phoenix, Md. 21131

[21] Appl. No.: 08/991,335

[22] Filed: Dec. 16, 1997

Related U.S. Application Data

[63] Continuation-in-part of application No. 08/847,191, May 1, 1997, and a continuation-in-part of application No. 08/847,186, May 1, 1997.

[51] Int. Cl.⁶ .................................................... A61B 17/00
[52] U.S. Cl. ............................................................ 606/144
[58] Field of Search ..................................... 606/144, 141, 606/143, 139, 146, 148, 147, 151

[56] References Cited

U.S. PATENT DOCUMENTS

| | | |
|---|---|---|
| 2,012,776 | 5/1935 | Roeder . |
| 2,162,297 | 4/1939 | Southerland et al. . |
| 2,227,270 | 1/1940 | Moore . |
| 2,610,631 | 11/1952 | Calicchio . |
| 2,856,933 | 10/1958 | Hildebrand et al. . |
| 3,033,204 | 5/1962 | Wood . |
| 3,870,048 | 3/1975 | Yoon . |
| 3,871,379 | 3/1975 | Clarke . |
| 3,911,923 | 10/1975 | Yoon . |
| 3,967,625 | 7/1976 | Yoon . |
| 3,985,138 | 10/1976 | Jarvik . |
| 3,989,049 | 11/1976 | Yoon . |
| 4,018,229 | 4/1977 | Komiya . |
| 4,085,743 | 4/1978 | Yoon . |
| 4,103,680 | 8/1978 | Yoon . |
| 4,177,813 | 12/1979 | Miller et al. . |
| 4,230,116 | 10/1980 | Watson . |
| 4,374,523 | 2/1983 | Yoon . |
| 4,471,766 | 9/1984 | Terayama . |
| 4,478,221 | 10/1984 | Heiss . |
| 4,773,420 | 9/1988 | Green . |
| 4,890,615 | 1/1990 | Caspari et al. . |
| 4,935,027 | 6/1990 | Yoon . |
| 5,037,433 | 8/1991 | Wilk et al. . |
| 5,059,201 | 10/1991 | Asnis . |
| 5,100,415 | 3/1992 | Hayhurst . |
| 5,144,961 | 9/1992 | Chen et al. . |
| 5,147,373 | 9/1992 | Ferzli . |
| 5,163,942 | 11/1992 | Rydell . |
| 5,181,919 | 1/1993 | Bergman et al. . |
| 5,196,022 | 3/1993 | Bilweis . |
| 5,217,030 | 6/1993 | Yoon . |
| 5,217,471 | 6/1993 | Burkhart . |
| 5,234,443 | 8/1993 | Phan et al. . |
| 5,236,434 | 8/1993 | Callicrate . |
| 5,242,459 | 9/1993 | Buelna . |
| 5,257,637 | 11/1993 | El Gazayerli . |
| 5,281,236 | 1/1994 | Bagnato et al. . |
| 5,281,238 | 1/1994 | Chin et al. . |
| 5,282,809 | 2/1994 | Kammerer et al. . |
| 5,290,284 | 3/1994 | Adair . |
| 5,300,078 | 4/1994 | Buelna . |
| 5,312,423 | 5/1994 | Rosenbluth et al. . |

(List continued on next page.)

FOREIGN PATENT DOCUMENTS

| | | |
|---|---|---|
| 0 477 020 | 3/1992 | European Pat. Off. . |
| 509 640 | 10/1930 | Germany . |

*Primary Examiner*—Michael Buiz
*Assistant Examiner*—Vikki Trinh

[57] ABSTRACT

A method of anatomical tissue ligation includes the steps of introducing a distal end of an anatomical tissue ligation instrument assembly at an internal operative site in a patient's body, grasping anatomical tissue at the internal operative site with a grasping member of the anatomical tissue ligation instrument assembly disposed at the distal end, positioning a contractible ligature loop formed of a length of filamentous ligature material of the anatomical tissue ligation instrument assembly around the anatomical tissue while the anatomical tissue remains grasped by the grasping member external of the distal end, contracting the ligature loop around the anatomical tissue to form a ligature and severing the length of ligature material proximally of the ligature to separate the ligature from the remainder of the length of ligature material.

26 Claims, 13 Drawing Sheets

U.S. PATENT DOCUMENTS

| | | |
|---|---|---|
| 5,334,199 | 8/1994 | Yoon . |
| 5,336,229 | 8/1994 | Noda . |
| 5,336,231 | 8/1994 | Adair . |
| 5,403,330 | 4/1995 | Tuason . |
| 5,403,331 | 4/1995 | Chesterfield et al. . |
| 5,405,351 | 4/1995 | Kinet et al. . |
| 5,417,684 | 5/1995 | Jackson et al. . |
| 5,423,834 | 6/1995 | Ahmed . |
| 5,466,241 | 11/1995 | Leroy et al. . |
| 5,486,186 | 1/1996 | Yoon . |
| 5,489,288 | 2/1996 | Buelna . |
| 5,507,797 | 4/1996 | Suzuki et al. . |
| 5,562,684 | 10/1996 | Kammerer . |
| 5,571,120 | 11/1996 | Yoon . |
| 5,609,597 | 3/1997 | Lehrer . |
| 5,658,299 | 8/1997 | Hart . |
| 5,681,332 | 10/1997 | Onuki . |
| 5,693,059 | 12/1997 | Yoon . |
| 5,704,943 | 1/1998 | Yoon et al. . |

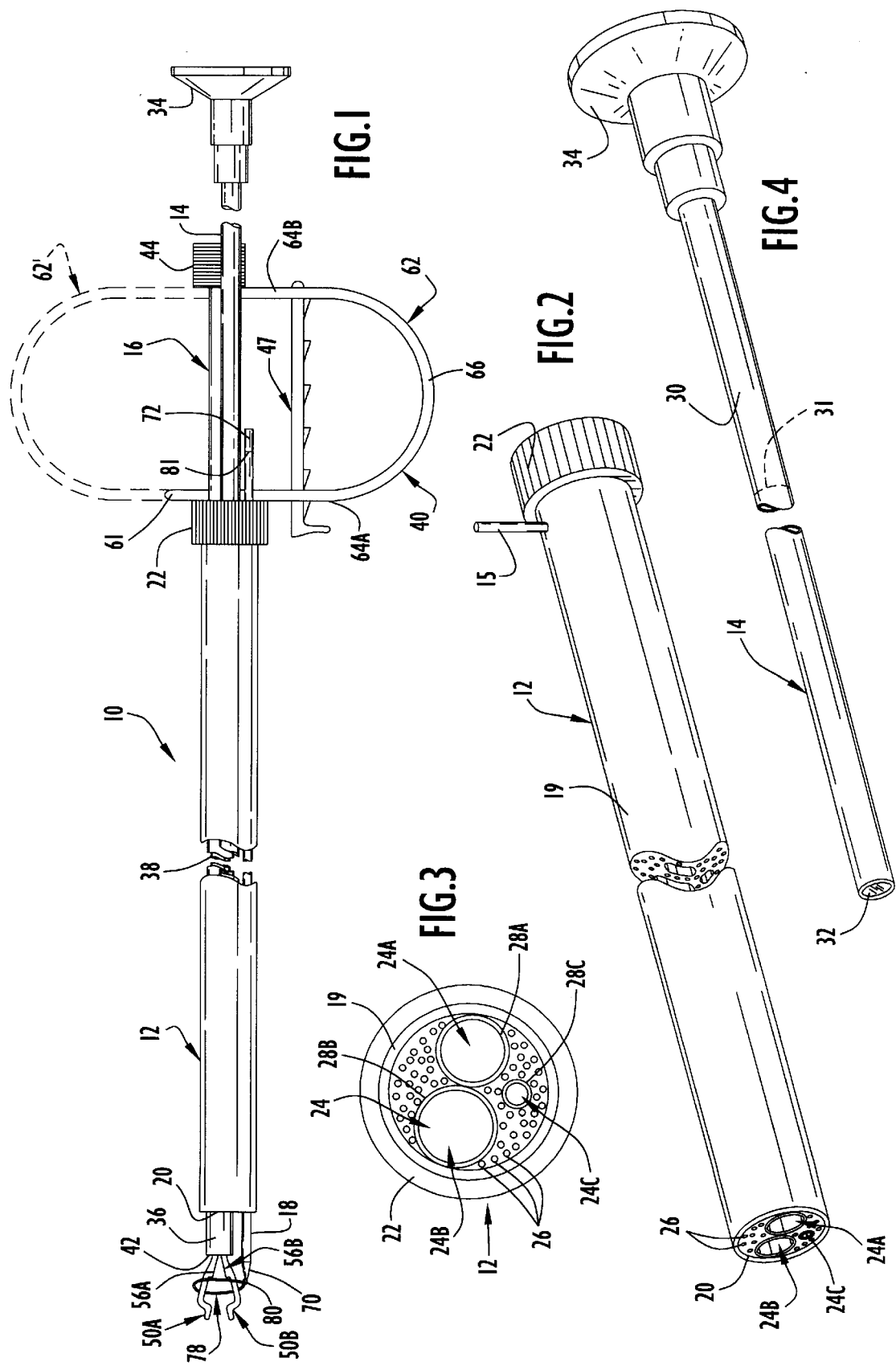

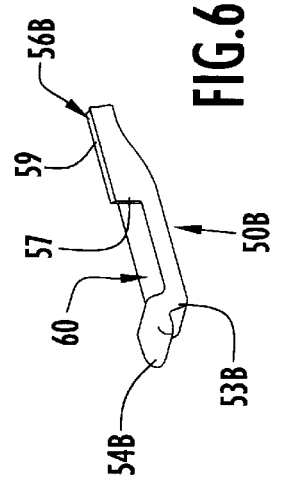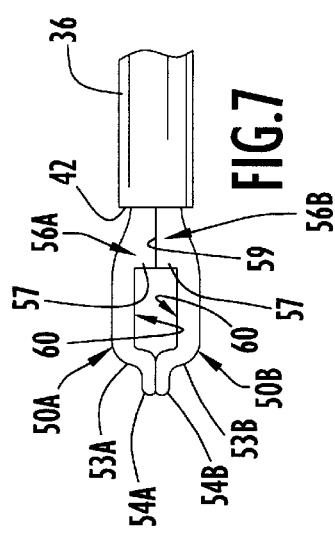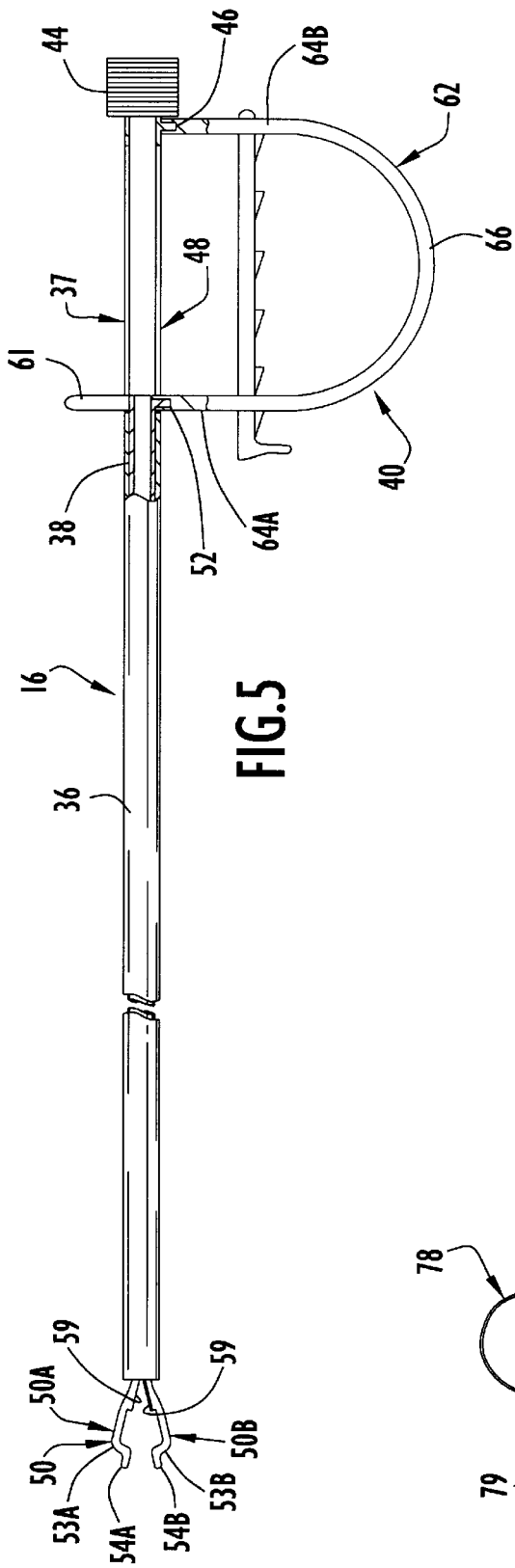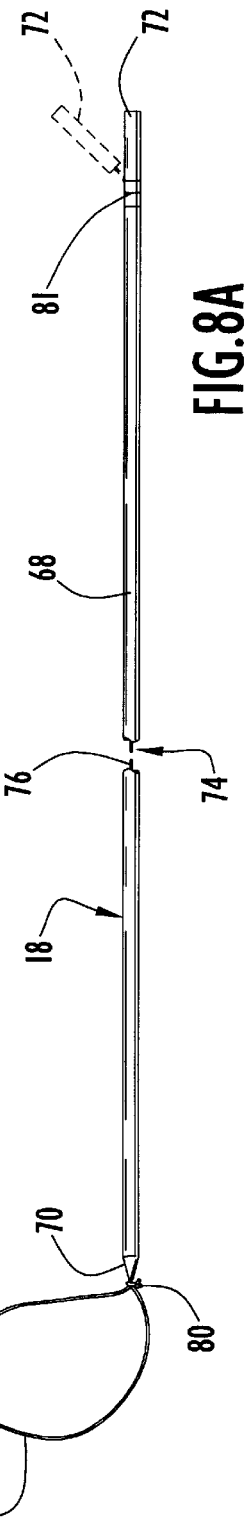

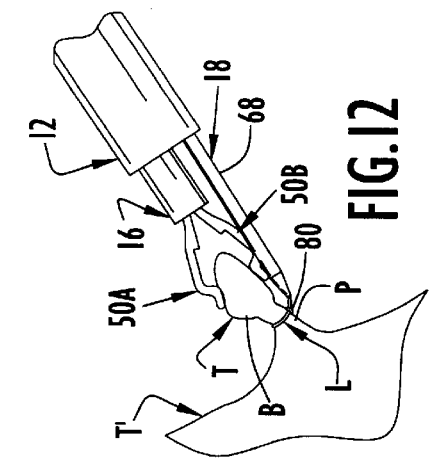
FIG.10
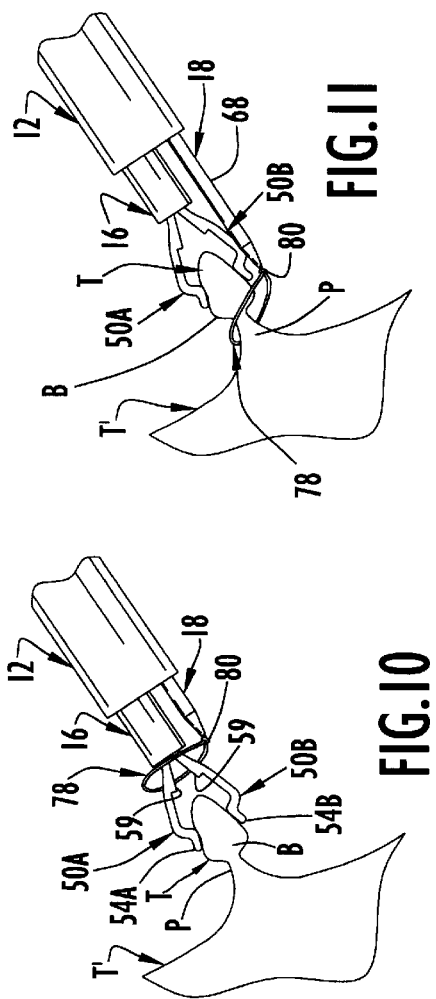
FIG.11
FIG.12
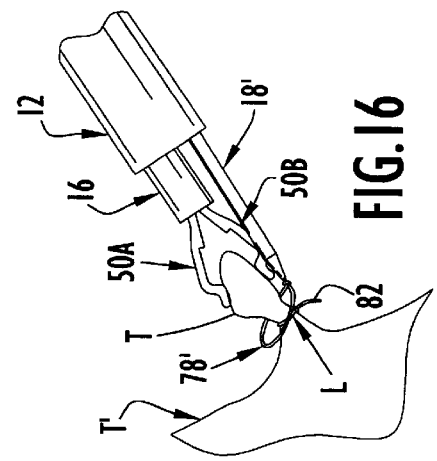
FIG.16
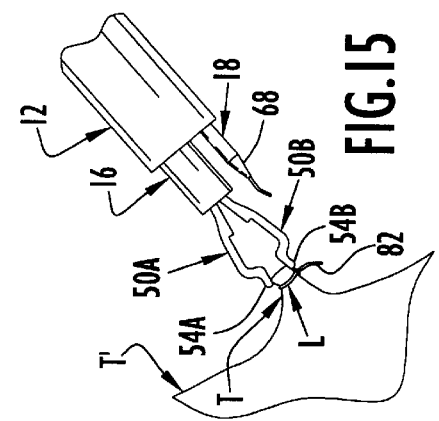
FIG.15
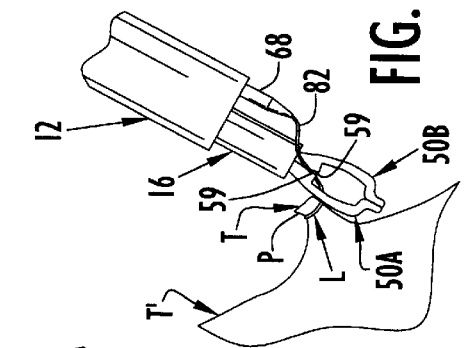
FIG.14
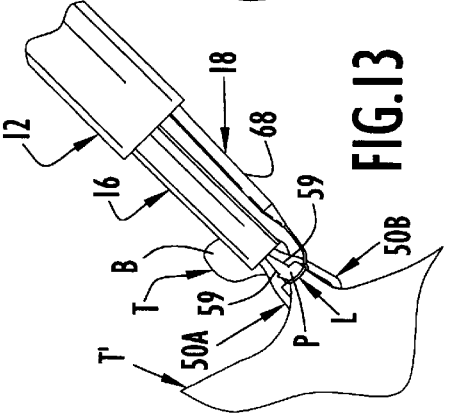
FIG.13

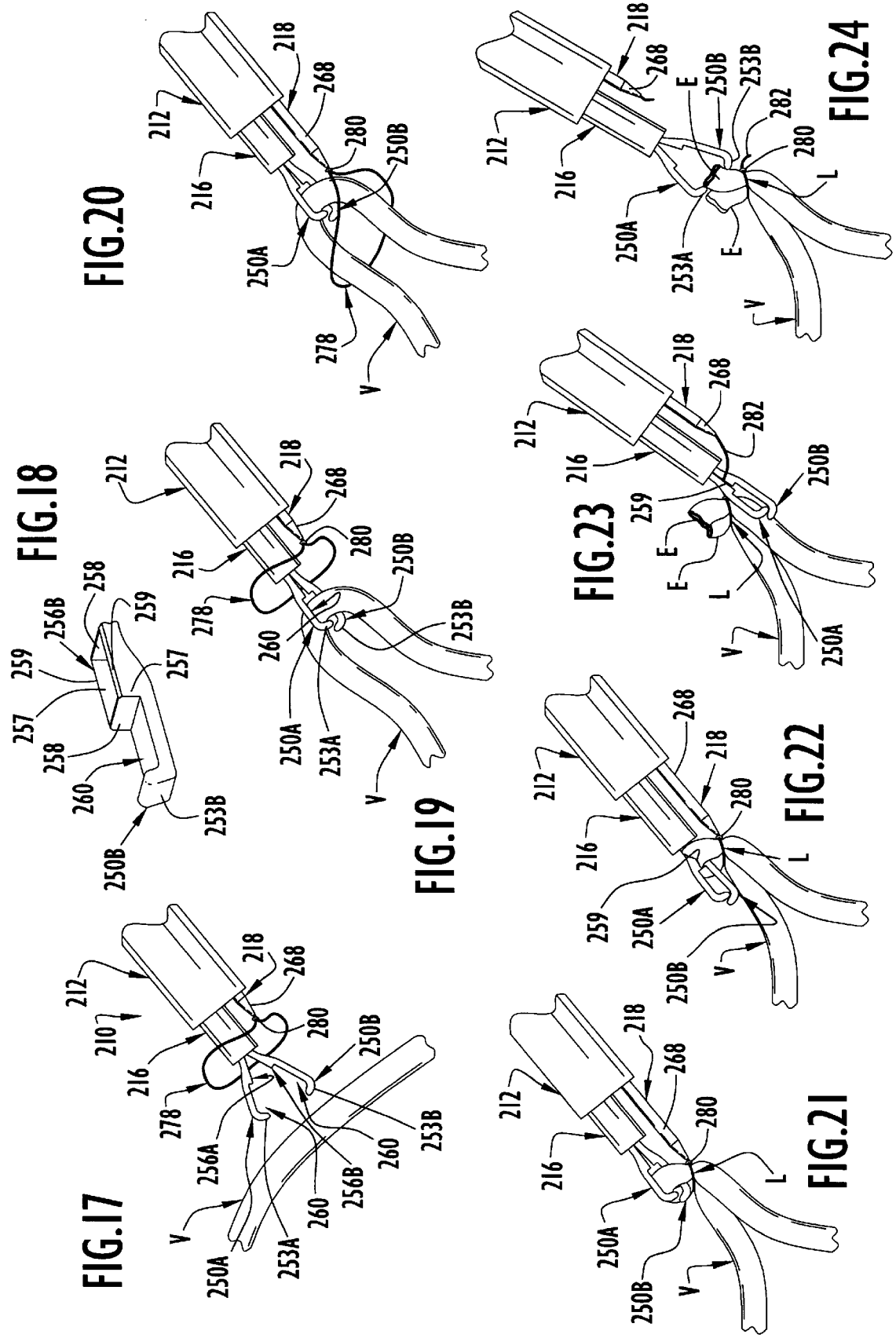

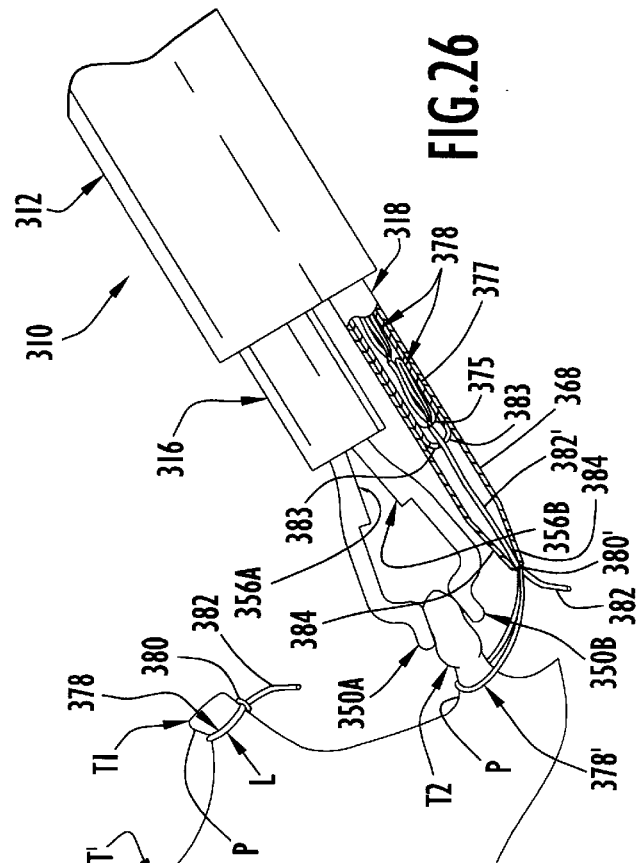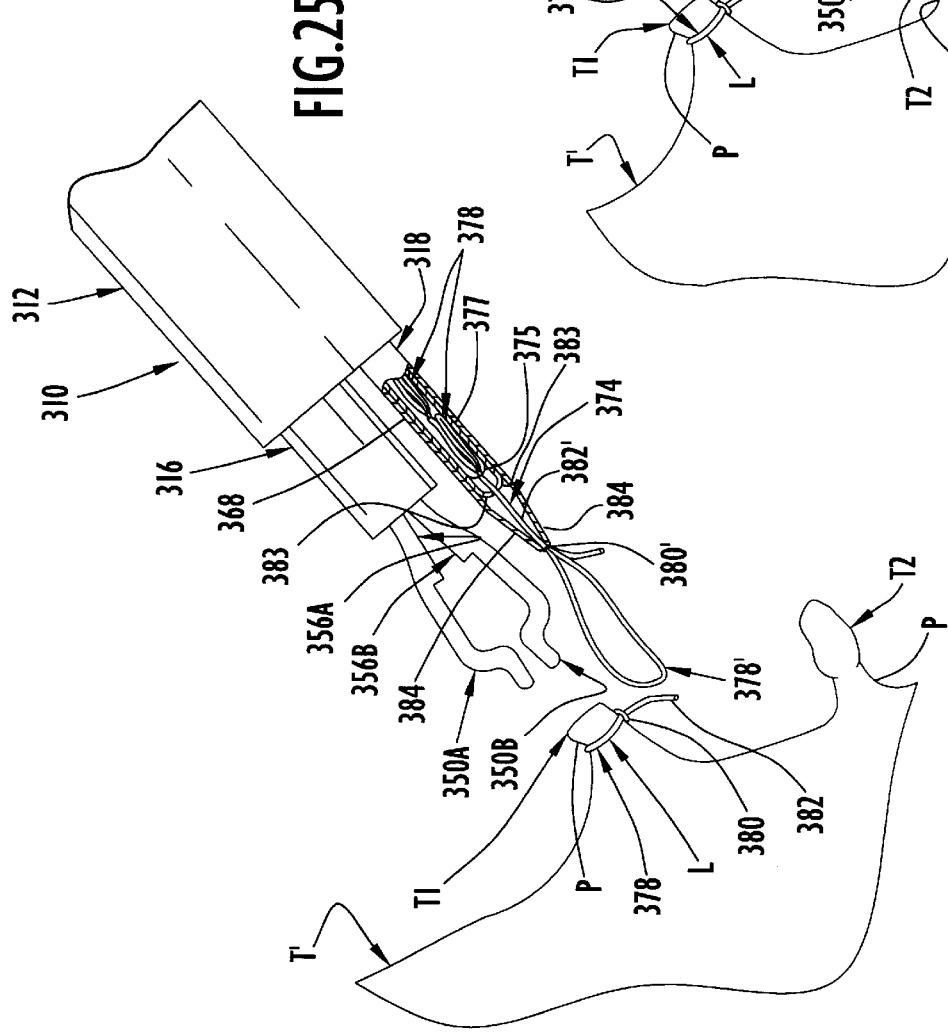

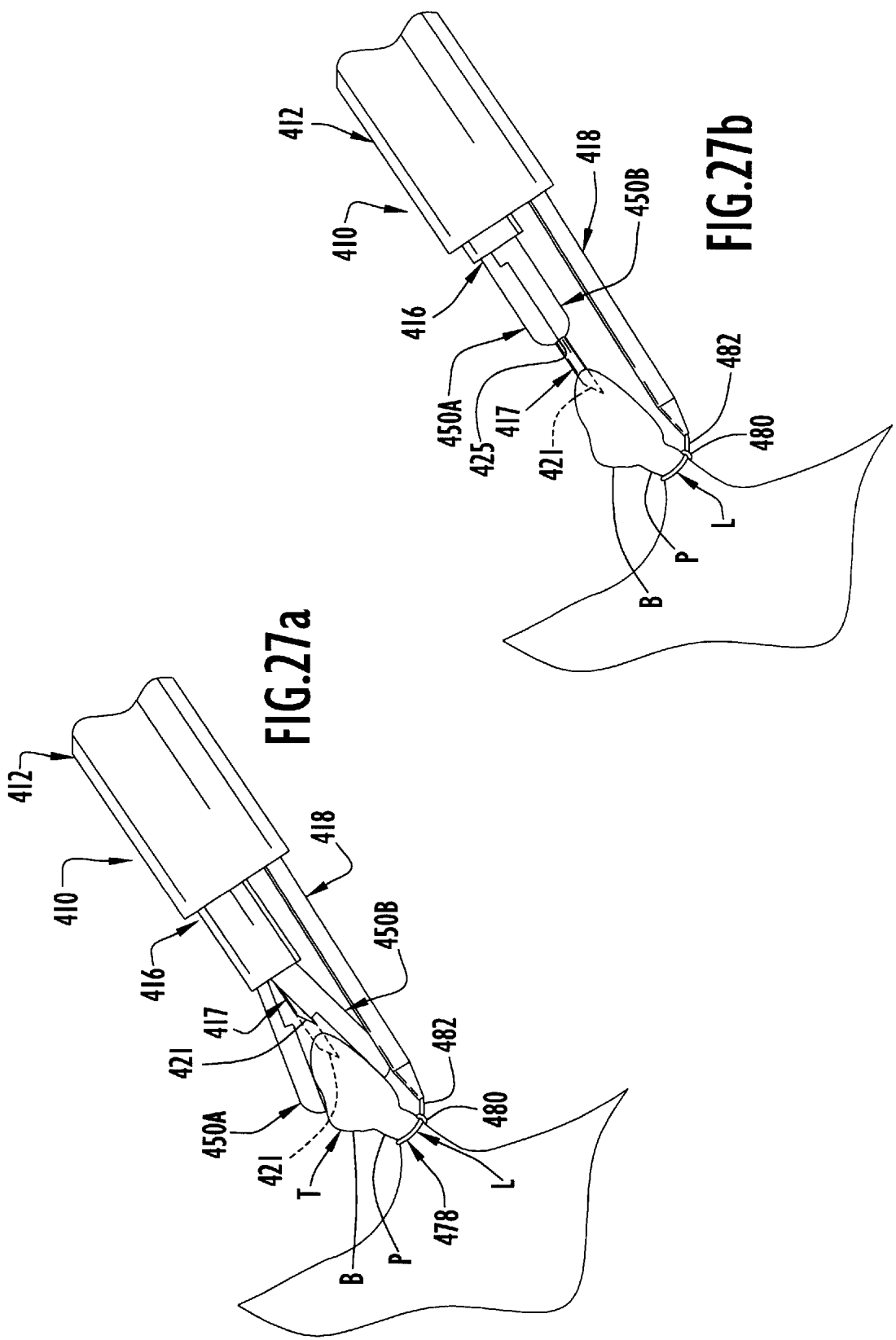

METHODS OF ANATOMICAL TISSUE LIGATION

CROSS-REFERENCE TO RELATED PATENT APPLICATIONS

This application is a continuation-in-part of prior application Ser. No. 08/847,191 filed May 1, 1997 and entitled Instrument Assemblies For Performing Anatomical Tissue Ligation and a continuation-in-part of prior application Ser. No. 08/847,186 filed May 1, 1997 and entitled Methods of Endoscopic Tubal Ligation, the disclosures of which are incorporated herein by reference.

BACKGROUND OF THE INVENTION

1. Field of the Invention

The present invention relates to methods of anatomical tissue ligation and, more particularly, to methods of ligating tubular and non-tubular anatomical tissue with a single instrument assembly.

2. Discussion of the Prior Art

Various operative procedures previously performed as open surgery requiring relatively large longitudinal incisions have come to be performed endoscopically. In endoscopic procedures, instruments are introduced at internal operative sites through relatively small, artificially created or natural openings providing communication with the internal operative sites from externally thereof. The instruments are manipulated remotely, from externally of the internal operative sites, to perform various operative procedures under visualization provided by an endoscope. Endoscopic procedures have many advantages over open surgical procedures including minimal invasiveness and trauma, shorter hospital stays and recovery times, minimal scarring and patient discomfort, fewer post-operative complications, lower cost and reduced risk for the patient.

Ligating anatomical tissue is a time consuming and tedious part of both endoscopic and open operative procedures due to the difficulty involved in applying an occluding ligature to anatomical tissue as is necessary and desirable in many various procedures. In particular, multiple, separate instruments are typically required to grasp the anatomical tissue and to position and contract a ligature loop therearound to form a ligature. Furthermore, additional instruments are usually required to cut the ligated anatomical tissue as well as the material of the ligature loop. Ligating anatomical tissue is particularly difficult in endoscopic procedures due to the restricted access to the internal operative sites and the limited room for maneuverability. Accordingly, the advantages of endoscopic procedures are sometimes outweighed by the disadvantages caused by the length of time required to perform endoscopic procedures where such time is significantly extended due to the time required for anatomical tissue ligation.

The use of endoscopic techniques for various operative procedures involving anatomical tissue ligation has been restricted, therefore, by a lack of instrumentation and by procedural difficulties due to the limited room for access, maneuverability and visualization at the internal operative sites and due to the need for various different instruments to be introduced at the internal operative sites. Accordingly, many operative procedures cannot be safely and efficiently performed as endoscopic or laparoscopic surgery and must be performed as open surgery with its attendant disadvantages.

SUMMARY OF THE INVENTION

Accordingly, it is a primary object of the present invention to overcome the disadvantages of prior art methods of anatomical tissue ligation.

The present invention has as another object to utilize a single instrument assembly to grasp anatomical tissue, to position a contractible ligature loop around the grasped anatomical tissue and to contract the ligature loop around the anatomical tissue to form a ligature.

Additionally, it is an object of the present invention to utilize a single instrument assembly to form a ligature in anatomical tissue and to sever the anatomical tissue proximally of the ligature to create a stump of anatomical tissue at the ligature.

A further object of the present invention is to ligate anatomical tissue with a ligature of filamentous material, to cut the anatomical tissue proximally of the ligature and to cut the filamentous material proximally of the ligature using a single instrument assembly.

An additional object of the present invention is to form a plurality of ligatures in anatomical tissue utilizing a grasper for grasping anatomical tissue and a plurality of ligating devices carried by the grasper, each ligating device having a contractible ligature loop and a knotting element maintained externally of an operating member for contracting the ligature loop.

It is also an object of the present invention to facilitate endoscopic anatomical tissue ligation to expand the types of operative procedures that can be performed endoscopically.

Another object of the present invention is to minimize the number and size of the ports needed to access an internal operative site in an endoscopic anatomical tissue ligation procedure.

A further object of the present invention is to perform anatomical tissue ligation endoscopically via a single port.

An additional object of the present invention is to minimize the size of a single port used to perform endoscopic anatomical tissue ligation.

Some of the advantages of the present invention are that various operations or procedural steps of anatomical tissue ligation normally requiring separate instruments can be performed utilizing fewer instruments or a single instrument assembly, the anatomical tissue ligation procedures according to the present invention can be performed with instrumentation operated with a single hand, the procedures of the present invention can be used to ligate peduncular anatomical structure, various anatomical structures can be ligated according to the present invention including polyps, cysts, fibroids, organs and tumors, anatomical tissue can be penetrated or punctured as part of the anatomical tissue ligation procedures, fluids can be drained from anatomical tissue as part of the anatomical tissue ligation procedures, anatomical tissue can be ligated with a desired tension as tactilely sensed by the surgeon, the taking of a biopsy sample or specimen of the anatomical tissue is facilitated, the need for general anesthesia can be avoided in endoscopic procedures with the use of small size ports made possible by the relatively small diametric or cross-sectional sizes of the instrument assemblies, anatomical tissue ligation can be performed endoscopically utilizing a single port or multiple ports, various procedures involving anatomical tissue ligation can be safely and effectively performed as miniaturized laparoscopic procedures, and various procedures and functions including irrigation, aspiration, supply of medicaments and other fluids, and transmission of energy such as electrical coagulation, cautery, laser, cryoenergy and ultrasound application can be carried out incidental to anatomical tissue ligation.

These and other objects, advantages and benefits are realized with the present invention as characterized in a method of anatomical tissue ligation comprising the steps of introducing a distal end of an anatomical tissue ligation instrument assembly at an internal operative site in a patient's body with a proximal end of the anatomical tissue ligation instrument assembly disposed external of the patient's body, grasping anatomical tissue at the internal operative site with a grasping member of the anatomical tissue ligation instrument assembly disposed at the distal end, positioning a contractible ligature loop formed of a length of filamentous ligature material of the anatomical tissue ligation instrument assembly around the grasped anatomical tissue, contracting the ligature loop around the grasped anatomical tissue, from the proximal end of the anatomical tissue ligation instrument assembly, to form a ligature, cutting the length of filamentous ligature material proximally of the ligature with the distal end of the anatomical tissue ligation instrument assembly to separate the ligature from the remainder of the length of ligature material and withdrawing the anatomical tissue ligation instrument assembly from the operative site leaving the ligature in the patient's body. The anatomical tissue can be severed or cut proximally of the ligature with the anatomical tissue ligation instrument assembly. Cutting members of the anatomical tissue ligation instrument assembly can be used to sever or cut the anatomical tissue, and the severed or cut anatomical tissue can be captured by the cutting members for removal of the severed or cut anatomical tissue from the patient's body.

Other objects and advantages of the present invention will become apparent from the following description of the preferred embodiments taken in conjunction with the accompanying drawings.

BRIEF DESCRIPTION OF THE DRAWINGS

FIG. 1 is a broken side view of an anatomical tissue ligation instrument assembly for use in the methods according to the present invention.

FIG. 2 is a broken perspective view of a passage defining member or barrel of the anatomical tissue ligation instrument assembly.

FIG. 3 is a distal end view of the passage defining member.

FIG. 4 is a broken perspective view of an endoscope of the anatomical tissue ligation instrument assembly.

FIG. 5 is a broken side view, partly in section, of a grasper of the anatomical tissue ligation instrument assembly.

FIG. 6 is a broken perspective view of a grasping member of the grasper.

FIG. 7 is a broken side view of a distal portion of the grasper showing the grasping members in a closed position.

FIG. 8A is a broken side view of a ligator of the anatomical tissue ligation instrument assembly.

FIG. 10 is a broken side view illustrating the grasping members moved toward the closed position to grasp the pedunculated tissue structure between the grasping members.

FIG. 11 is a broken side view illustrating a contractible ligature loop of filamentous ligature material of the ligator positioned around the pedicle of the pedunculated tissue structure.

FIG. 12 is a broken side view illustrating contraction of the ligature loop around the pedicle of the pedunculated tissue structure to form a ligature.

FIG. 13 is a broken side view illustrating the tissue structure being cut proximally of the ligature to form a stump of anatomical tissue at the ligature.

FIG. 14 is a broken side view showing the ligature material being cut proximally of the ligature to release the ligature from the ligator.

FIG. 15 is a broken side view illustrating use of the anatomical tissue ligation instrument assembly to cauterize the stump.

FIG. 16 is a broken side view of the grasping members grasping the ligated pedunculated tissue structure prior to cutting thereof and illustrating another contractible ligature loop being placed around the pedunculated tissue structure for use in forming a second ligature.

FIG. 17 is a broken side view of a distal end of a second modified anatomical tissue ligation instrument assembly with the grasping members thereof in the open position to receive a blood vessel therebetween.

FIG. 18 is a broken perspective view of a grasping member of the grasper for the second modified anatomical tissue ligation instrument assembly.

FIG. 19 is a broken side view showing the grasping members of the second modified anatomical tissue ligation instrument assembly in the closed position grasping the blood vessel therebetween and drawing the blood vessel into a loop formation.

FIG. 20 is a broken side view showing a contractible ligature loop of filamentous ligature material of the second modified anatomical tissue ligation instrument assembly positioned around the loop formation of the blood vessel.

FIG. 21 is a broken side view illustrating the ligature loop contracted around the loop formation of the blood vessel to form a ligature.

FIG. 22 is a broken side view showing a segment of the loop formation being cut proximally of the ligature to form two ends of the blood vessel extending from the ligature.

FIG. 23 is a broken side view showing the ligature material being cut proximally of the ligature.

FIG. 24 is a broken side view illustrating cautery of the ends of the blood vessel.

FIG. 25 is a broken side view, partly in section, of a third modified anatomical tissue ligation instrument assembly illustrating deployment of a second contractible ligature loop of a multiple loop ligature supply of the ligator of the third modified anatomical tissue ligation instrument assembly following formation of a ligature in an anatomical structure with a first contractible ligature loop of the ligator.

FIG. 26 is a broken side view, partly in section, depicting use of the second contractible ligature loop to form a ligature in another anatomical structure.

FIG. 27a is a broken side view of a fourth modified anatomical tissue ligation instrument assembly used to ligate an anatomical structure and showing a penetrating member of the fourth modified anatomical tissue ligation instrument assembly partially extended to penetrate the anatomical structure.

FIG. 27b is a broken side view of the fourth modified anatomical tissue ligation instrument assembly used to ligate an anatomical structure and showing the penetrating member of the fourth modified anatomical tissue ligation instrument assembly fully extended to penetrate the anatomical structure.

DESCRIPTION OF THE PREFERRED EMBODIMENTS

Figure 8B:
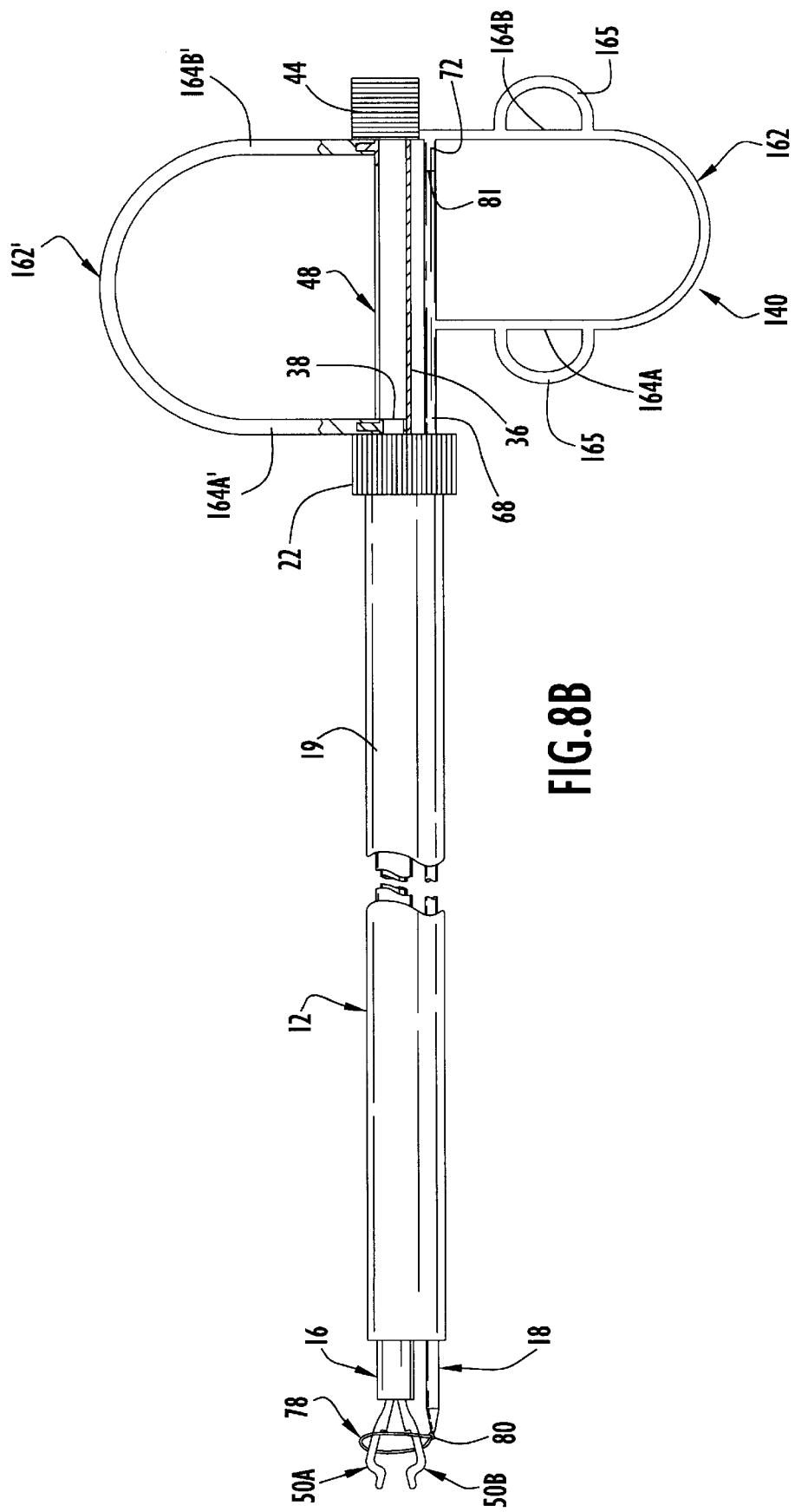
FIG. 8B is a broken side view, partly in section, of a first modified anatomical tissue ligation instrument assembly for use in the methods of the present invention.

An anatomical tissue ligation instrument assembly for use in the methods of anatomical tissue ligation according to the present invention is illustrated at 10 in FIG. 1. Anatomical tissue ligation instrument assembly 10 is similar to that disclosed in prior application Ser. No. 08/847,191 and Ser. No. 08/847,186 incorporated herein by reference. Anatomical tissue ligation instrument assembly 10 includes an elongate passage or channel defining member, platform or barrel 12 and an endoscope 14, a grasping instrument or grasper 16 and a ligating instrument, ligating device or ligator 18 disposed in barrel 12. As shown in FIG. 2, barrel 12 includes an elongate, hollow cylindrical or tubular member 19 terminating distally at a distal end 20 for being disposed at an internal operative site in a patient's body, typically within an anatomical cavity, and terminating proximally at a proximal end for being disposed externally of the internal operative site, such as externally of the anatomical cavity or externally of the patient's body. A diametrically enlarged cylindrical collar 22 is disposed on the proximal end of the tubular member 19 and has longitudinally extending external grooves to facilitate grasping. As shown in FIGS. 2 and 3, barrel 12 includes a plurality of channels or passages 24 extending longitudinally through tubular member 19. Barrel 12 has three parallel channels 24A, 24B and 24C of different diametric or cross-sectional sizes corresponding to the external diametric or cross-sectional sizes of endoscope 14, grasping instrument 16 and ligating instrument 18, respectively. However, the barrel 12 can have one or more additional channels for receiving one or more additional instruments to be introduced at the internal operative site and/or for fluid flow therethrough. One or more light transmitting elements, such as a plurality of light transmitting fibers 26, extend longitudinally through the tubular member 19 and are disposed in the space between an inner surface of tubular member 19 and the channels 24A, 24B and 24C. In the case of barrel 12, the channels 24A, 24B and 24C are formed by thin wall, hollow cylindrical or tubular sleeves 28A, 28B and 28C, respectively, extending longitudinally through the tubular member 19 with the light transmitting fibers 26 being disposed externally of sleeves 28A, 28B and 28C in the space between the sleeves 28A, 28B and 28C and the inner surface of tubular member 19. The sleeves 28A, 28B and 28C are preferably arranged closely or compactly in tubular member 19 to minimize the external diametric or cross-sectional size of barrel 12. For example, one or more of the sleeves 28A, 28B and 28C can have its periphery in contact with or touching the inner surface of tubular member 19, as shown in FIG. 3 for sleeves 28A and 28B, and/or one or more of the sleeves 28A, 28B and 28C can have its periphery in contact with or touching the periphery of another sleeve, as shown in FIG. 3 for sleeves 28A and 28B. The sleeves 28A, 28B and 28C can be fixedly secured in barrel 12, such as by being adhesively affixed or attached to one another, to the tubular member 19 and/or to the light transmitting fibers 26. The light transmitting fibers 26 can completely fill the space between the sleeves and the barrel. Channels 24 can be defined in tubular member 19 without sleeves to further reduce the external diametric or cross-sectional size of barrel 12. For instance, light transmitting fibers 26 can be arranged in tubular member 19 to define channels 24, and the inner surface of tubular member 19 can define peripheral or circumferential segments of one or more of the channels 24. Light transmitting fibers 26 are designed to transmit light from a light source (not shown) to the distal end 20 to provide illumination at the internal operative site, and the barrel 12 can have a light coupler 15 connectible with a light source, the light coupler not being shown in FIGS. 1, 3 and 9.

Endoscope 14, which can be rigid or flexible or partly rigid and partly flexible, includes an elongate, cylindrical body 30 having an image receiver or observation window 32 at a distal end thereof and a viewing device 34, such as an eyepiece, at a proximal end thereof as shown in FIG. 4. As shown by way of example in FIG. 4, the body 30 is divided into a first or distal segment and a second or proximal segment at a junction 31, the second segment carrying the eyepiece. The first segment can be flexible while the second segment is rigid or vice versa. The body 30 houses optics or a viewing system, such as various lenses, mirrors and/or fiber optics, optically coupling image receiver 32 with the viewing device 34 for transmitting an image from image receiver 32 to viewing device 34. The eyepiece for endoscope 14 is axially aligned with body 30; however, it should be appreciated that the eyepiece can be offset from the body 30 or not axially aligned therewith and can be angularly adjustable as disclosed in application Ser. No. 08/847,191, incorporated herein by reference. Where the eyepiece is offset from the body 30, the eyepiece can be offset from the body 30 parallel with or at various angles to the body 30. The first segment can be longer than the second segment, and the second segment can be pivotally mounted to the first segment for pivotal or angular movement relative to the first segment to adjust the angle or position of viewing device 34. The viewing device can include a video monitor, and the endoscope 14 can be designed to transmit an image from observation window 32 for viewing on the video monitor.

As shown in FIG. 5, grasping instrument or grasper 16 includes an elongate, hollow or tubular outer member 36, an elongate inner member 38 disposed within outer member 36 and a handle 40 mounting proximal ends of the outer and inner members. Outer member 36 has a distal end 42 and a proximal end mounted to a diametrically enlarged, cylindrical collar 44 disposed proximally of handle 40 and provided with circumferentially extending external grooves to facilitate grasping. A transverse ear or flange 46 is disposed on the outer member 36 distally of collar 44, and a slot 48 is formed in outer member 36 longitudinally or axially aligned with ear 46 and extending longitudinally, distally therefrom.

Inner member 38 has a distal end carrying or formed as at least one grasping, engaging or jaw member 50 and a proximal end provided with a transverse ear or flange 52 for being disposed in slot 48. Inner member 38 has opposed grasping members 50A and 50B including inwardly curved or angled distal segments 53A and 53B, respectively, and distal tips, ends or fingers 54A and 54B extending distally from distal segments 53A and 53B, respectively. Grasping members 50A and 50B carry inwardly protruding cutting members 56A and 56B, respectively, spaced proximally from respective distal segments 53A and 53B. Each cutting member includes one or more cutting edges or blades for cutting anatomical tissue. As shown in FIG. 6 for grasping member 50B, cutting members 56A and 56B each have an inwardly protruding longitudinal side wall 57 extending lengthwise along one lateral side of the associated grasping member and a cutting edge 59 along an inner edge of the side wall 57. The side walls 57 and cutting edges 59 are proximally spaced from the distal segments 53A and 53B, respectively, such that a recess or space 60 is defined by each grasping member distally of its cutting member. Accordingly, each grasping member has a cutting edge 59 extending longitudinally along one side thereof, and the cutting edges 59 are on the same side of the grasping members in opposition to one another to cooperate with one another to cut anatomical tissue therebetween when the cutting members are moved to a cutting position as explained further below. The cutting edge of one grasping member can abut the cutting edge of the opposed grasping member in edge to edge fashion when the cutting members are in the cutting position or the cutting edges can overlap one another in the cutting position as shown in FIG. 7. For example, the longitudinal side wall 57 of grasping member 50A protrudes inwardly farther than the side wall 57 of grasping member 50B to fit inside of or overlap the side wall 57 of grasping member 50B in the cutting position for cutting members 56A and 56B such that the cutting edges 59 move past one another to cut anatomical tissue therebetween. Depending on procedural use, one or more additional longitudinal and/or transverse side walls can carry or be formed with additional cutting edges, and the cutting members can be designed as biopsy boxes.

Grasping members 50A and 50B are normally disposed in an open or non-grasping position as shown in FIG. 5 wherein the grasping members extend angularly outwardly away from one another. Tip 54A and cutting member 56A of grasping member 50A are spaced from tip 54B and cutting member 56B of grasping member 50B to allow anatomical tissue to be received between the grasping members; and, accordingly, the cutting members are in a non-cutting position. Grasping members 50A and 50B are movable inwardly toward one another, i.e. in the direction of a longitudinal axis of the inner member 38, from the open position to a closed or grasping position wherein tips 54A and 54B are disposed closer to one another than they are in the open position. FIG. 7 illustrates grasping members 50A and 50B in a fully closed position with tips 54A and 54B in contact or abutment and the cutting members 56A and 56B in a cutting position with the cutting edge 59 of cutting member 56A moved past the cutting edge 59 of cutting member 56B.

The grasping members can be designed in many various ways to be normally disposed in the open position and to be movable to a closed position and back to the open position. The grasping members can be biased toward the open position. For example, the grasping members can be made entirely or partly of resilient or flexible materials or materials having shape memory, such as spring materials, to be resiliently biased toward the open position while being movable to a closed position and back to the open position. The grasping members can contact one another or not contact one another in the fully closed position. For example, the tips of the grasping members can abut one another in "kissing" fashion, can overlap one another or can be spaced from one another when the grasping members are in the fully closed position. In the case of grasping members 50A and 50B, the tips 54A and 54B abut one another in "kissing" fashion in the fully closed position. The cutting edges can be designed to abut one another in edge to edge fashion in the cutting position, or the cutting edges can be designed to move past or overlap one another in the cutting position. Anatomical tissue disposed between the grasping members distally of the cutting members will be grasped or held between the grasping members when the grasping members are in a closed position; and, anatomical tissue positioned between the cutting members will be cut by the cutting edges when the cutting members are in the cutting position. The distal tips of the grasping members can have various configurations including bent, hook-like and spoon-like shapes for picking up and/or lifting anatomical tissue as well as "kissing" tips as shown for tips 54A and 54B. The inner member 38 is preferably hollow or tubular as shown in FIG. 5 to allow fluid flow therethrough and/or to allow instruments to be introduced at and withdrawn from the internal operative site through the lumen of the inner member via the collar 44 and the proximal end of the outer member 36.

The grasping instrument 16 can be designed to supply energy to anatomical tissue to treat the tissue. For example, grasping instrument 16 can be provided with an electrical connector 61 coupled with inner member 38 as shown in FIGS. 1 and 5, in which case the inner member 38 and grasping members 50A and 50B are made of electrically conductive material. Electrical connector 61 is adapted to be connected with a source of electric current for transmission of electricity via the inner member 38 to treat anatomical tissue contacted by grasping members 50A and 50B, such as for electrical cautery or coagulation. Where the inner member 38 is designed to transmit electricity, it is preferable that the outer member 36 be made of electrically insulative material. As shown in FIG. 5, the outer member has an additional longitudinal slot 37 through which connector 61 extends, the slot 37 permitting longitudinal movement of the outer member 36 and/or the inner member 38 relative to the other since the connector 61 is slidable along the slot 37. In addition, it is desirable that the grasping instrument 16 be longitudinally movable relative to barrel 12 such that the distal end of the grasping instrument can be retracted or drawn into the barrel for safety and protection, and it is preferable that the barrel be made of electrically insulative material. It should be appreciated that the grasping instrument can be designed to transmit various forms of energy including electricity, laser, ultrasound and cryoenergy.

Handle 40 comprises a U-shaped hand grip 62 having a distal leg 64A connected to ear 52, a proximal leg 64B connected to ear 46 and a curved base 66 connecting the proximal and distal legs. As shown in FIG. 5, an upper end of proximal leg 64B is formed with a recess for receiving ear 46, and an upper end of distal leg 64A is formed with a recess for receiving ear 52 to connect the handle 40 to the outer and inner members. Handle 40 is made partly or entirely of resilient or flexible materials or materials having shape memory, such as spring materials, to maintain grasping instrument 16 in a rest position as shown in FIG. 5 wherein outer member 36 is in a proximal longitudinal position relative to grasping members 50A and 50B with the grasping members 50A and 50B disposed in the open position beyond the outer member distal end 42. Handle 40 can be manually compressed or squeezed to move the outer member 36 and/or the inner member 38 relative to the other such that the outer member is in a distal longitudinal position relative to grasping members 50A and 50B causing the grasping members 50A and 50B to be moved inwardly toward one another toward the fully closed position shown in FIG. 7. The distal end 42 of the outer member in the distal longitudinal position is closer to tips 54A and 54B than it is in the proximal longitudinal position such that the grasping members are moved to the fully closed position or to a less than fully closed or partially closed position due to engagement or constraint by the outer member. The grasping members will be moved to the fully closed position when the outer member and/or the inner member is/are moved from the rest position a first amount, as achieved with squeezing operation of handle 40. The grasping members will be moved to a partially closed or less than fully closed position when the outer member 36 and/or inner member 38 is/are moved from the rest position less than the first amount, as achieved with less squeezing force on the handle 40. Depending on the size and/or configuration of the anatomical tissue to be grasped, the tissue can be grasped by the grasping members in the fully closed position or in a partially closed position, and tissue can be held or captured in the recesses or spaces 60. Release of the manual compressive or squeezing force on handle 40 causes the grasping instrument to return to the rest position due to the resilient bias of handle 40. If desired, handle 40 can include bilateral hand grips as represented by additional U-shaped hand grip 62' shown in dotted lines in FIG. 1. Handle 40 preferably includes a locking mechanism 47 for locking the handle 40 in various compressed positions and/or in a spread position, the locking mechanism 47 being of the type described in applicant's prior application Ser. No. 08/694,385, filed Aug. 8, 1996 and incorporated herein by reference.

It should be appreciated that the cutting members do not have to be in the cutting position when the grasping members are in the fully closed position. Accordingly, the grasping members can be designed for movement from the fully closed position to a further closed position to move the cutting members to the cutting position. The outer member 36 and/or inner member 38 can be moved from the rest position a second amount, greater than the first amount, to move the grasping members 50A and 50B to a further closed position corresponding to the cutting position for the cutting members 56A and 56B. The further closed position can be obtained by squeezing handle 40 with greater force than that required for the fully closed position.

One example of a ligating instrument, ligating device or ligator 18 for use in the methods of the present invention is illustrated in FIG. 8A and comprises a ligating device of the type called an Endoloop™ made by Ethicon Endo-Surgery, Inc. The ligating instrument 18 includes an elongate tubular member, operating member or pusher 68 having a tapered distal end 70, a proximal end 72 and a ligature supply 74 carried by tubular member 68. Ligature supply 74 includes a length of filamentous ligature material 76, which can be bioabsorbable, extending through the lumen of tubular member 68 and having a distal end pre-formed into a variable size or contractible, closed ligature loop 78 and a proximal end secured to the proximal end 72 of tubular member 68. Distal end 70 has a hole or aperture therein communicating with the lumen of tubular member 68, and the ligature material 76 slidably passes through the aperture such that the ligature loop 78 is disposed externally of the distal end 70. Ligature loop 78 includes a loop segment 79 of ligature material 76 and a knotting element 80. Knotting element 80 for ligature loop 78 is in the form of a knot, such as a slip or hangman's knot or other such pretied slidable knot, formed in the ligature material 76 and through which the length of ligature material 76 slidably passes. The ligature loop 78 is a closed loop with the loop segment 79 extending between the knotting element 80 with no breaks or separations therebetween. The knotting element 80 is larger in size than the hole or aperture in distal end 70 and cannot pass therethrough. The proximal end 72 of the tubular member 68 is breakable or frangible such that it can be separated or broken off from the remainder of the tubular member 68 at a break point 81 as shown in dotted lines in FIG. 8A to permit the ligature material 76 and the tubular member 68 to be moved longitudinally relative to one another. Accordingly, the ligature material 76 can be pulled proximally through the lumen of tubular member 68 to contract or reduce the size of loop segment 79 as the knotting element 80 remains externally of distal end 70 and/or the tubular member 68 can be moved or pushed distally along the length of ligature material 76 to move or push knotting element 80 therealong to contract the loop segment 79.

It should be appreciated that the ligating instrument 18 and the grasping instrument 16 can both be operated by a single handle 140 as illustrated in FIG. 8B. Handle 140 illustrated in FIG. 8B includes bilateral U-shaped hand grips 162 and 162', the handgrip 162' having distal and proximal legs 164A' and 164B', respectively, connected to the inner member 38 and the outer member 36, respectively, of the grasping instrument 16 as described above for handgrip 62, the distal leg 164A' being slidable in longitudinal slot 48 formed in outer member 36. The handgrip 162 has a proximal leg 164B secured to collar 44 and a distal leg 164A secured to the tubular member 68 of the ligating instrument 18. The proximal end 72 of the tubular member 68 is secured to the proximal leg 164B. The hand grip 162 of FIG. 8B is made partly or entirely of resilient materials allowing legs 164A and 164B to be manually spread apart from one another from the rest position shown in FIG. 8B as facilitated by finger rings 165. Accordingly, when the proximal end 72 is separated from the remainder of the tubular member 68 at the break point 81, spreading operation of hand grip 162 causes the tubular member 68 to be moved distally and/or the length of ligature material to be moved proximally to contract the ligature loop 78. Release of the manual spreading force on hand grip 162 causes the hand grip 162 to return to the rest position. Either or both of the hand grips 162 and 162' can be provided with a locking mechanism for locking the hand grips in a compressed position and/or a spread position.

The anatomical tissue ligation instrument assembly 10 is assembled or arranged as shown in FIG. 1 with endoscope 14 disposed in channel 24A, grasping instrument 16 disposed in channel 24B and ligating instrument 18 disposed in channel 24C of barrel 12. Endoscope 14 is disposed in channel 24A with image receiver 32 aligned with the distal end 20 of the barrel and with viewing device 34 disposed proximally of handle 40. If desired, the endoscope 14 can be provided with a stop or abutment to limit or control the forward distance that the endoscope can be inserted in the barrel. If desired, the endoscope can be introduced through the barrel to position the image receiver 32 distally of the distal end 20 of the barrel and can be slidable relative to the barrel to adjust the longitudinal position of the endoscope prior to or during use to facilitate visualization of the internal operative site. The endoscope and/or the barrel can be provided with a releasable locking mechanism to selectively fix or secure the position of the endoscope relative to the barrel. The viewing device 34, i.e. the eyepiece, should be spaced from the handle 40 a distance sufficient to prevent contamination between the eyepiece and the handle, such distance preferably being in the range of 5–10 cm.

Grasping instrument 16 is disposed in channel 24B with the distal leg 64A of handle 40 in abutment with the collar 22 of the barrel such that the grasping members 50A and 50B in the open or non-grasping position protrude distally beyond the distal end 20 of the barrel. To permit insertion of the grasping instrument 16 through channel 24B, the grasping members 50A and 50B are moved to the fully closed position via squeezing operation of handle 40; and, once the grasping members 50A and 50B are disposed externally of barrel 12, release of handle 40 will return the grasping instrument to the rest position such that the grasping members are again in the open or non-grasping position. The ligating instrument 18 is disposed in barrel 12 with the distal end 70 thereof disposed distally of the distal end 20 of barrel 12 with the ligature loop 78 disposed around the grasping instrument 16 such that the grasping members protrude distally through the ligature loop 78. It is not necessary, however, for the ligature loop 78 to be disposed around the grasping instrument. The proximal end 72 of the tubular member 68 is attached to the remainder of tubular member 68 at break point 81, the proximal end 72 and break point 81 being disposed proximally of the collar 22 of barrel 12 and alongside handle 40.

In the case of anatomical tissue ligation instrument assembly 10, endoscope 14, grasping instrument 16 and ligating instrument 18 are each capable, individually, of longitudinal sliding movement relative to barrel 12; however, it should be appreciated that any or all of endoscope 14, grasping instrument 16 and ligating instrument 18 can be fixed or non-movable relative to barrel 12 except for that movement required for operation of the respective instruments. In the case of anatomical tissue ligation instrument assembly 10, the outer member 36 of grasping instrument 16 protrudes distally beyond the distal end 20 of barrel 12 when the grasping instrument 16 is fully inserted in the barrel with handle 40 in abutment with collar 22; however, it should be appreciated that the outer member 36 need not protrude beyond the barrel 12 when the grasping instrument is fully inserted therein. By sizing the channels 24A, 24B and 24C to closely correspond to the external peripheral or cross sectional sizes of the endoscope 14, the grasping instrument 16 and the ligating instrument 18, respectively, the endoscope, the grasping instrument and the ligating instrument can be frictionally held in the barrel to resist movement while being capable of movement relative to the barrel in response to a manual force sufficient to overcome the frictional holding force.

Anatomical tissue can be ligated in accordance with the present invention in open procedures, closed or endoscopic procedures and mini-lap procedures. In endoscopic procedures, one or more narrow or small size ports or passages in the patient's body are utilized to access an internal operative site, such as an operative site in an anatomical cavity, the one or more ports or passages providing communication with the internal operative site from external thereof, such as external of the anatomical cavity. The diametric or cross sectional size of the one or more ports or passages is preferably no larger than necessary to receive or accommodate instruments to be used during the procedure. Preferably, the diametric or cross sectional size of the one or more ports is minimized to allow the endoscopic procedure to be performed utilizing local anesthesia and non-hospital sites. The number of ports will be dependent on whether the instruments to be utilized are to be introduced through a single port or through multiple ports. The ports can be artificially created openings or incisions or natural anatomical openings or passages.

The one or more ports can be established conventionally in an endoscopic procedure by penetrating an anatomical cavity wall, such as the abdominal wall, to access an anatomical cavity, such as the abdomen, and introducing insufflation gas in the anatomical cavity to create a pneumoperitoneum. Typically, a small diameter hollow needle is utilized to penetrate the anatomical cavity wall and to introduce gas, such as carbon dioxide or nitrous oxide, into the anatomical cavity to create the pneumoperitoneum, thusly expanding the anatomical cavity for visualization and access. The needle is withdrawn and a larger diameter penetrating instrument, typically including a penetrating member or trocar disposed in a portal sleeve or cannula, is introduced through the opening formed by the needle to introduce a distal end of the portal sleeve in the abdominal cavity. The trocar is withdrawn from the portal sleeve leaving the portal sleeve in place to extend through the anatomical cavity wall to provide a port or passage therethrough establishing communication with the anatomical cavity from external thereof. Instruments including an endoscope, a laparoscope or other remote viewing device can be introduced in the anatomical cavity through the port or passage of the portal sleeve; and, where multiple portal sleeves are installed, instruments can be introduced through any and all of the portal sleeves. The various instruments introduced through the one or more ports have their distal ends positioned in the anatomical cavity and their proximal ends positioned external of the anatomical cavity allowing the instruments to be manipulated, operated and/or maneuvered via their proximal ends under visualization provided external of the anatomical cavity by the endoscope.

Figure 9:
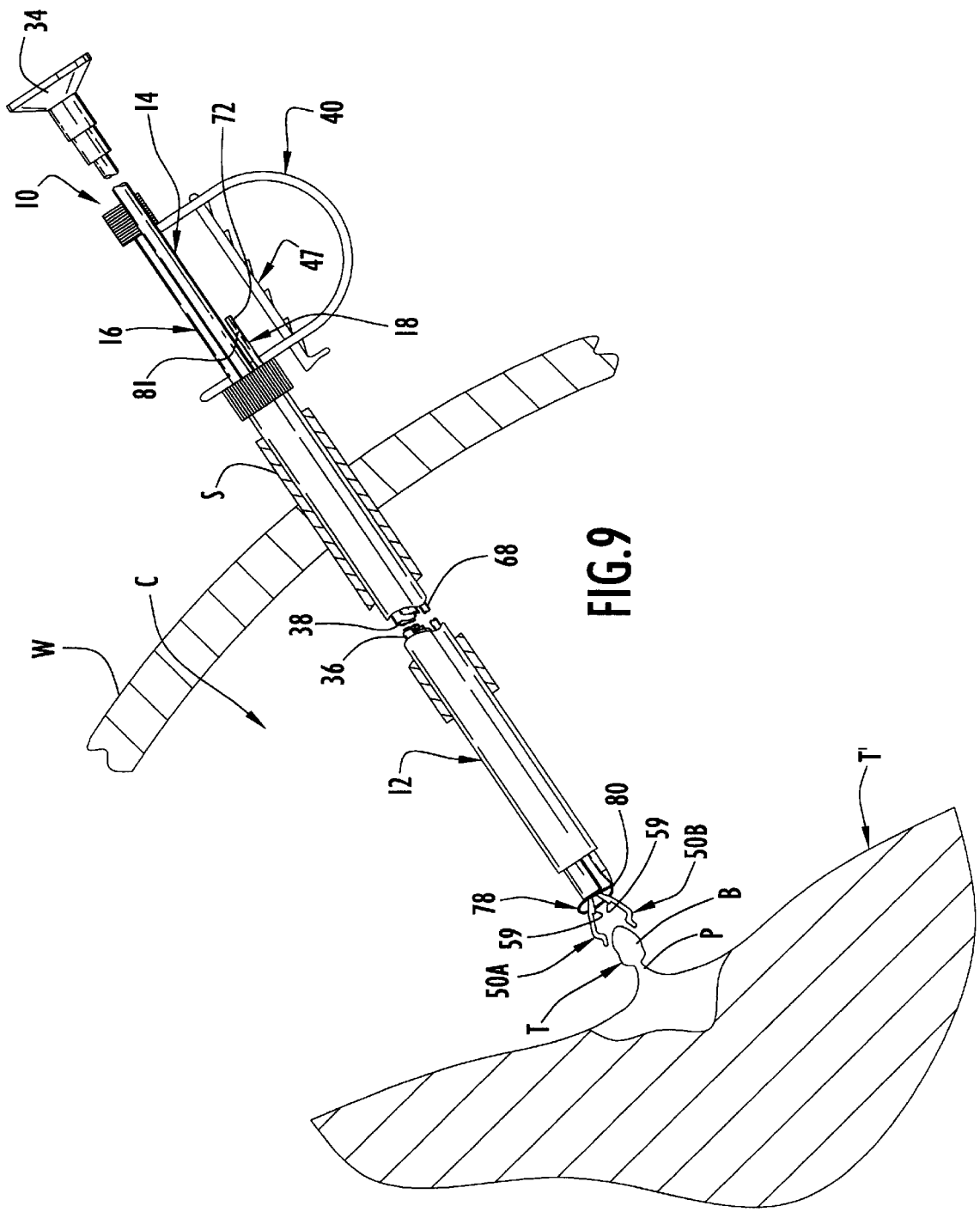
FIG. 9 is a broken side view, partly in section, of the anatomical tissue ligation instrument assembly of FIG. 1 introduced through a port in an anatomical cavity wall with the grasping members in the open position to receive a pedunculated tissue structure therebetween in a single port endoscopic procedure.

In a single port endoscopic procedure of anatomical tissue ligation according to the present invention, a distal end of the anatomical tissue ligation instrument assembly 10 is introduced at an internal operative site in a patient's body, such as in the abdominal cavity C, through a relatively small size port or passage providing communication with the internal operative site from external thereof as shown in FIG. 9. FIG. 9 illustrates anatomical tissue ligation instrument assembly 10 extending through a portal sleeve or cannula S disposed in an opening through a wall W of the abdominal cavity C with a proximal end of the instrument assembly 10 disposed external of the abdominal cavity C, i.e. external of wall W. Since it is important to maintain the pneumoperitoneum, the portal sleeve or cannula S is typically provided with a gaseous seal preventing the ingress and egress of fluids to and from the cavity C when the anatomical tissue ligation instrument assembly 10 is withdrawn from sleeve S and does not pass therethrough. Various gaseous seals can be provided for the portal sleeve or cannula S including gaseous seals for sealingly engaging instruments or instrument assemblies of various sizes introduced through the portal sleeve S.

As shown in FIG. 9, the opening in wall W is no larger than necessary to accommodate the cross sectional size of portal sleeve S, and the portal sleeve S is no larger than necessary to accommodate the cross sectional size of instrument assembly 10 to minimize the cross sectional size of the port needed to access the anatomical cavity C. Accordingly, the grasping members 50A and 50B will typically be in the fully closed position when the anatomical tissue ligation instrument assembly 10 is introduced at the internal operative site through the portal sleeve S to permit passage of the instrument assembly through the portal sleeve. The fully closed position for the grasping members 50A and 50B is obtained via squeezing operation of handle 40, and the grasping members can be locked in the fully closed position via the locking mechanism 47. By minimizing the cross sectional size of the opening in wall W, the need for general anesthesia can be avoided allowing the procedure to be performed endoscopically under local anesthesia in non-hospital sites. Illumination of the anatomical cavity C is provided by light transmitting fibers 26 of barrel 12, which transmit light from a light source coupled with barrel 12 via light connector 15. The anatomical cavity C and the procedures performed therein are visualized, from external of the cavity wall W, with the endoscope 14 via the viewing device 34.

Once a distal end of anatomical tissue ligation instrument assembly 10 has been introduced in the anatomical cavity C, the instrument assembly 10 is manipulated external of the anatomical cavity C to receive anatomical tissue to be ligated between the grasping members 50A and 50B. "Anatomical tissue" as used herein is intended to include anatomical tissue, structure, formations or organs such as polyps, cysts, appendages, organs, fibroids, peduncular anatomical structures, tubular and non-tubular anatomical structures, growths and tumors. FIG. 9 illustrates the grasping members 50A and 50B moved to the open position via release of handle 40 from the compressed position and return of handle 40 to the rest position following introduction of the distal end of the anatomical tissue ligation instrument assembly in the anatomical cavity C. The grasping members 50A and 50B are positioned on opposite sides of the anatomical tissue to be ligated, such as pedunculated tissue structure T including a tissue body B and a narrower pedicle, peduncle, base or stem P connecting body B to another anatomical structure, tissue or part T'. Pedunculated tissue structure T can include various anatomical formations, tissue, structure, organs, fibroids, polyps, organs, such as the gall bladder, tumors and growths. As shown in FIG. 9, grasping members 50A and 50B are positioned on opposite sides of tissue body B with tissue body B disposed forwardly or distally of cutting edges 59. Grasping member 50B can support the tissue body B and can be used to pick up the pedunculated tissue structure T. Once the grasping members 50A and 50B have been positioned to receive the pedunculated tissue structure T therebetween, handle 40 is compressed to move the grasping members 50A and 50B from the open position to a closed or grasping position as shown in FIG. 10 such that the tissue body B is held between the grasping members 50A and 50B. As shown in FIG. 10, the tips 54A and 54B of the grasping members contact the tissue body B and thusly firmly hold or grasp the pedunculated tissue structure T. The compressive holding or grasping force exerted by the grasping members 50A and 50B on the pedunculated tissue structure T can be controlled by controlling the extent to which the handle 40 is squeezed or compressed. The locking mechanism 47 permits incremental squeezing operation of the handle 40 with automatic locking of the handle 40 in incremental squeezed positions for controlled grasping of the pedunculated tissue structure T with desired force as tactilely sensed by the surgeon through squeezing operation of the handle 40.

The ligating instrument 18 is moved distally relative to the grasping instrument 16 and/or the grasping instrument 16 is moved proximally relative to the ligating instrument 18, depending on the rigidity of the tissue being ligated and the extent to which its position in the cavity C is fixed, to position the ligature loop 78 around the pedunculated tissue structure T, which remains held by the grasping members 50A and 50B. FIG. 11 shows the ligating instrument 18 moved distally relative to grasping instrument 16 to position the ligature loop 78 around the pedicle P of the pedunculated tissue structure T. The ligature loop 78 can be positioned to encircle the pedunculated tissue structure T at various locations in accordance with a desired site for ligating the pedunculated tissue structure T as determined by the surgeon. In the illustrated procedure, the ligature loop 78 is positioned to ligate the pedicle P close to the anatomical structure T'.

Once the ligature loop 78 has been properly positioned around the anatomical tissue to be ligated, the proximal end 72 of the tubular member 68 is broken or separated from the remainder of the tubular member 68 at breakpoint 81. The tubular member 68 is moved longitudinally, distally along the length of ligature material while the proximal end 72 is held external of the anatomical cavity C to push or move knotting element 80 distally toward the pedunculated tissue structure T to contract or reduce the size of the loop segment around the pedicle P to form a ligature L as shown in FIG. 12, the tubular member 68 being moved longitudinally, distally relative to the grasping instrument 16. Alternatively and/or in addition to distal movement of tubular member 68, the freed or unattached proximal end 72, which is secured to the length of ligature material, can be pulled proximally relative to the tubular member 68 causing the length of ligature material to be moved longitudinally, proximally relative to and through the tubular member 68 as the knotting element 80 remains held externally of the distal end of tubular member 68 to contract the loop segment around the pedicle P to form the ligature L. The ligature loop 78 is contracted or reduced in size around the pedicle P until a desired tension has been obtained for the ligature L as can be tactilely sensed or felt by the surgeon at the proximal end of the ligating instrument 18.

Once the pedunculated tissue structure T has been ligated to the desired tension, handle 40 is released for movement toward the rest position causing the grasping members 50A and 50B to move from the closed or grasping position toward the open or non-grasping position. Depending on the nature of the ligated anatomical tissue and/or the procedure being performed, the ligated anatomical tissue may not need to be cut or severed from the ligature. However, it may be desirable and/or necessary in many cases to sever the anatomical tissue proximally of or away from the ligature and to remove the severed anatomical tissue from the patient's body. In order to sever a selected or desired portion of the pedunculated tissue structure T proximally of the ligature L, the grasping instrument 16 is manipulated to receive a selected portion of the pedunculated tissue structure T between the grasping members 50A and 50B in alignment with the cutting edges 59. If necessary, the pedunculated tissue structure T can be manipulated via the length of ligature material to maneuver the ligature L and facilitate positioning of the selected tissue portion between the cutting edges 59. As shown in FIG. 13, a portion of the pedicle P between the ligature L and the tissue body B is aligned with the cutting edges 59. The grasping members 50A and 50B are moved toward the fully closed position via compression of handle 40 to move the cutting members to the cutting position causing the pedicle portion to be cut or severed by cutting edges 59 proximally of the ligature L as shown in FIG. 13. Accordingly, a stump of pedunculated tissue structure T is created at the ligature L, the stump being shown in FIGS. 14 and 15. The cut portion or segment of pedunculated tissue structure T will remain held by the cutting members, the cut portion or segment including part of pedicle P and the entire tissue body B. The grasping instrument 16 is withdrawn from the abdominal cavity C, via withdrawal of the grasping instrument 16 from the barrel 12, for removal and retrieval of the cut portion or segment external of the patient's body.

The grasping instrument 16 is reintroduced in the abdominal cavity C via the barrel 12, and the tubular member 68 is moved proximally or backed away from the ligature L to present a segment 82 of ligature material extending proximally from the ligature L. Anatomical tissue ligation instrument assembly 10 is manipulated to receive the segment 82 between grasping members 50A and 50B in the open position, with the segment 82 in alignment with cutting edges 59. Handle 40 is compressed to move the grasping members 50A and 50B toward the fully closed position thereby moving the cutting members to the cutting position causing the cutting edges 59 to cut the segment 82 of ligature material proximally of the ligature L as shown in FIG. 14. Accordingly, the ligature L will be severed from the remainder of the ligature supply allowing the ligating instrument 18 to be withdrawn from the cavity C.

The anatomical tissue ligation instrument assembly 10 can be used to treat anatomical tissue at the internal operative site with energy. For example, FIG. 15 illustrates the grasping members 50A and 50B grasping the stump of tissue structure T therebetween with electricity being supplied to the stump via the tips 54A and 54B of the grasping members 50A and 50B for electric cautery to control bleeding.

The ligating instrument 18 can be withdrawn from barrel 12, and another ligating instrument 18 can be inserted in barrel 12 for introduction in the abdominal cavity C for use in forming another ligature. The ligating instrument 18 can be withdrawn from the barrel 12 while the barrel 12 remains in the portal sleeve S or the entire anatomical tissue ligation instrument assembly 10 can be withdrawn from the portal sleeve S and reintroduced in the anatomical cavity with another ligating instrument disposed in the barrel. If desired, more than one ligature can be formed in the anatomical tissue, pedunculated tissue structure T in the illustrated procedure, for redundant protection. Where multiple ligatures are formed in the anatomical tissue, the ligatures can be placed next to, on top of one another or spaced from one another.

FIG. 16 illustrates pedunculated tissue structure T subsequent to formation of ligature L with segment 82 of the ligature material cut proximally of ligature L prior to cutting of tissue structure T proximally of ligature L. Another ligating instrument 18' has been introduced through barrel 12, and the ligature loop 78' of ligating instrument 18' has been placed over the tissue structure T for use in forming a second ligature. The ligature loop 78' is shown placed on top of the ligature L to form a second ligature on top of the ligature L. Upon formation of one or more ligatures with anatomical tissue ligation instrument assembly 10, the instrument assembly 10 is withdrawn from the anatomical cavity C leaving the one or more ligatures in place in the cavity C.

Another procedure of anatomical tissue ligation according to the present invention is illustrated in FIGS. 17–24, which illustrate ligation of a tubular anatomical structure and, in particular, a blood vessel V. FIG. 17 shows a distal end of an anatomical tissue ligation instrument assembly 210, similar to instrument assembly 10, positioned at an operative site with grasping members 250A and 250B of grasping instrument 216 of instrument assembly 210 disposed in the open position on opposite sides of blood vessel V. Grasping members 250A and 250B are similar to grasping members 50A and 50B except that the distal segments 253A and 253B of the grasping members 250A and 250B, respectively, define distal ends or tips for the grasping members 250A and 250B, respectively. The cutting members 256A and 256B for grasping members 250A and 250B are different from cutting members 56A and 56B in that the cutting members 256A and 256B are biopsy boxes. Cutting members 256A and 256B are similar to the cutting members disclosed in prior application Ser. No. 08/847,191 and Ser. No. 08/847,186 incorporated herein by reference. As shown in FIG. 18 for grasping member 250B and cutting member 256B, cutting member 256B is formed by a pair of inwardly protruding longitudinal side walls 257 connected to one another by inwardly protruding transverse side walls 258 to form or define a box. The longitudinal side walls 257 carry or are formed with cutting edges 259, respectively, the cutting edges 259 extending lengthwise along opposed lateral sides of the grasping member 250B. The transverse side walls 258 extend perpendicularly between the cutting edges 259, the transverse side walls 258 being disposed at distal and proximal ends of the cutting edges 259, respectively. The cutting members 256A and 256B are proximally spaced from the distal segments 253A and 253B, respectively, such that spaces or recesses 260 are defined between the distal segments 253A and 253B and the cutting members 256A and 256B, respectively. The cutting members 256A and 256B cooperate with one another to cut anatomical tissue therebetween when the cutting members 256A and 256B are in a cutting position as explained further below. The cutting edges 259 of one grasping member can abut the cutting edges 259 of the other grasping member when the cutting members 256A and 256B are in the cutting position, or the cutting edges of one grasping member can overlap the cutting edges of the other grasping member when the cutting members are in the cutting position. For example, one of the biopsy boxes can be made smaller than the other to nest or fit within the larger size box as shown for cutting members 256A and 256B, the biopsy box of cutting member 256A being smaller than that for cutting member 256B. Depending on procedural use, the transverse side walls 258 can carry or be formed as cutting edges.

Grasping members 250A and 250B are disposed in the open position shown in FIG. 17 when the handle (not shown) therefor is not compressed as described for grasping instrument 16. With the grasping members 250A and 250B in the open position, the cutting members 256A and 256B are spaced from one another to be disposed in the non-cutting position. The blood vessel V is received between the grasping members 250A and 250B with the blood vessel V extending in a direction transverse to a longitudinal axis of the grasping instrument 216 in alignment with recesses 260.

The grasping members 250A and 250B are moved from the open position to the fully closed or grasping position via squeezing operation of the handle to grasp, capture or hold the blood vessel V between the grasping members 250A and 250B as shown in FIG. 19, the blood vessel V being disposed in recesses 260. One of the grasping members 250A or 250B is longer than the other such that the distal segments 253A and 253B overlap when the grasping members 250A and 250B are in the fully closed position, the grasping member 250B being longer than the grasping member 250A. The entire instrument assembly 210 is moved proximally, or the grasping instrument 216 is moved proximally relative to the rest of the instrument assembly 210, to draw the blood vessel V into a loop formation, knuckle, or bend as shown in FIG. 19.

The ligating instrument 218 for instrument assembly 210 is the same as the ligating instrument 18, and the ligature loop 278 of ligating instrument 218 is disposed around the grasping instrument 216 prior to the grasping members 250A and 250B being used to grasp the blood vessel V as shown in FIG. 17. Once the blood vessel V has been drawn into the loop formation, the ligating instrument 218 is moved distally relative to the rest of the instrument assembly 210 to position the ligature loop 278 around the loop formation of blood vessel V as shown in FIG. 20. The ligature loop 278 is moved distally off of the grasping members 250A and 250B and is advanced distally over the loop formation such that the loop formation protrudes through the ligature loop 278. As discussed above for instrument assembly 10, the ligature loop 278 need not be disposed around the grasping instrument 216 when the instrument assembly 210 is introduced at the operative site in which case the ligature loop 278 is placed over the blood vessel V, and the grasping members 250A and 250B are thereafter moved through the ligature loop to pick up and grasp the blood vessel V therethrough. The length of the loop formation that is drawn through the ligature loop 278 can be adjusted, controlled or selected by the surgeon in accordance with a desired site or location for a ligature to be formed in the loop formation of blood vessel V.

Once the ligature loop 278 has been properly positioned around the loop formation, the ligature loop 278 is contracted by moving the tubular member 268 longitudinally, distally along the length of ligature material to push or move knotting element 280 distally toward the loop formation to form a ligature L as shown in FIG. 21, the tubular member 268 being moved longitudinally, distally relative to the rest of the instrument assembly 210. The ligature loop 278 is contracted or reduced in size around the loop formation until a desired tension has been obtained for the ligature L as tactilely sensed or felt by the surgeon. Where cutting or severing of the blood vessel V proximally of the ligature L is not necessary, the segment of the ligature material extending from the ligature L is severed proximally of the ligature L to sever the ligature L from the remainder of the ligature supply. The ligature material is cut or severed utilizing the cutting members 256A and 256B as explained below. The anatomical tissue ligation instrument assembly 210 is then withdrawn from the operative site leaving the ligature L in place in the patient's body.

Where it is desired to sever the loop formation proximally of the ligature L, the loop formation is received between the cutting members 256A and 256B with the grasping members 250A and 250B in the open position. A segment of the loop formation to be cut is aligned with the cutting members 256A and 256B, and the grasping members 250A and 250B are moved to the fully closed position via the handle causing the cutting members 256A and 256B to be moved to the cutting position to cut the segment of the loop formation as shown in FIG. 22, which shows the loop formation being cut prior to the ligature L being severed from the remainder of the ligature supply. The blood vessel V is cut by cutting edges 259 at longitudinally spaced locations, and the cut segment of the blood vessel V between the longitudinally spaced locations is retained within the biopsy boxes, which are arranged one inside the other. Accordingly, two free ends E of blood vessel V are formed proximally of the ligature L as shown in FIG. 23. The grasping instrument 216 is withdrawn from the operative site for retrieval of the cut segment externally of the patient's body allowing the cut segment to be examined and analyzed.

The ligature material is cut proximally of the ligature L by positioning a segment 282 of the ligature material extending proximally from the ligature L between the grasping members 250A and 250B in the open position with the segment 282 in alignment with the cutting members 256A and 256B. The grasping members 250A and 250B are moved to the closed position causing the segment 282 of ligature material to be cut by the cutting edges 259 since the cutting members 256A and 256B are moved to the cutting position as shown in FIG. 23. Accordingly, the ligature L is severed from the remainder of the ligature supply allowing the instrument assembly 210 to be withdrawn from the operative site leaving the ligature L in the patient's body.

FIG. 24 illustrates electric cautery of the ends E with the instrument assembly 210 to control bleeding. Grasping members 250A and 250B are shown contacting one of the ends E to cauterize the contacted end E when the grasping members 250A and 250B are supplied with electric current as discussed above for instrument assembly 10. Upon completion of the ligation procedure on blood vessel V including any necessary or desired cutting of the blood vessel and/or treatment of the blood vessel V with energy, the instrument assembly 210 is withdrawn from the operative site and removed from the patient's body.

Another method of anatomical tissue ligation according to the present invention is illustrated in FIG. 25 and is representative of a procedure wherein a plurality of ligatures are formed at an operative site without withdrawing the ligating instrument from the patient's body. Anatomical tissue ligation instrument assembly 310 shown in FIG. 25 is similar to the anatomical tissue ligation instrument assembly 10 and includes barrel 312, grasping instrument 316, ligator 318 and a remote viewing device (not shown). Barrel 312 and grasping instrument 316 are similar to barrel 12 and grasping instrument 16, respectively. Ligator 318 is different from ligating instrument 18 in that the ligator 318 includes a multiple loop ligature supply 374 disposed in tubular member 368 and comprising a plurality of preformed, interconnected, contractible ligature loops 378 selectively deployable external of the tubular member 368. The ligator 318 is the same as that described in the prior application Ser. No. 08/847,191 incorporated herein by reference and includes an actuator 375 carrying multiple loop ligature supply 374 and a jaw member 377 disposed in tubular member 368 and housing the actuator 375. The jaw member 377 has jaws 383 at a distal end thereof movable between open and closed positions in response to longitudinal movement of actuator 375 and/or jaw member 377 relative to the other. The distal end of tubular member 368 comprises a plurality of push fingers 384 movable between contracted and expanded positions to allow the jaw member 377 to pass distally through the tubular member 368. A handle (not shown) at a proximal end of the ligator 318 is operable to move the tubular member 368 proximally relative to the jaw member 377 causing the push fingers to expand or spread in the expanded position such that the jaws 383 are positioned distally of the tubular member 368. The handle is operable to move the actuator 375 longitudinally, distally relative to the jaw member 377 causing the jaws 383 to be moved to the open position and causing the actuator 375 to pass distally through the jaw member 377. The ligature supply 374 is carried with the actuator 375 and is advanced distally by the actuator to position a ligature loop thereof externally of the jaws 383. Release of the handle causes the actuator 375 to move longitudinally, proximally relative to the jaw member 377 leaving the ligature supply 374 in its distally advanced position. The jaws 383 return to the closed position, and the tubular member 368 is moved distally to proximally engage the knotting element of the now externally deployed ligature loop. The jaws 383 have sharpened edges for cutting the segments 382 of ligature material extending between and connecting the ligature loops 378 as disclosed in the prior application incorporated herein by reference.

FIG. 25 illustrates a distal end of instrument assembly 310 introduced at an operative site, such as through a sleeve (not shown) extending through an opening in an anatomical cavity wall in a single port endoscopic procedure. FIG. 25 illustrates a pedunculated tissue structure T1 ligated along the pedicle P thereof with a ligature loop 378 of the ligature supply 374 to form a ligature L and the connecting segment 382 extending proximally from the ligature L cut with the edges of jaws 383 to sever the ligature L from the remainder of the ligature supply 374. The tissue structure TI is illustrated in FIG. 25 following cutting of the tissue structure T1 proximally of the ligature L with the cutting members 356A and 356B of grasping members 350A and 350B, respectively, of grasping instrument 316 as described above for instrument assembly 10. The ligator 318 is operated via the handle to deploy another ligature loop 378' external of tubular member 368 for use in forming another ligature without withdrawing the ligator 318 from the operative site, the ligator 318 being operated in the manner discussed above and disclosed in detail in the prior application Ser. No. 08/847,191 incorporated herein by reference.

FIG. 26 illustrates the grasping members 350A and 350B of grasper 316 grasping another pedunculated tissue structure T2 at the operative site with the ligature loop 378' positioned around the pedicle P of tissue structure T2. FIG. 26 shows the tubular member 368 being moved distally toward the tissue structure T2 to move the knotting element 380' of ligature loop 378' in a direction to contract the ligature loop 378' around the pedicle P to form another ligature.

A method of forming a ligature in anatomical tissue including penetration of the anatomical tissue is illustrated in FIGS. 27a and 27b. An anatomical tissue ligation instrument assembly 410 illustrated in FIGS. 27a and 27b is similar to anatomical tissue ligation instrument assembly 10 and includes barrel 412, grasper 416 and ligating instrument 418. Barrel 412 and ligating instrument 418 are similar to barrel 12 and ligating instrument 18. Grasper 416 for instrument assembly 410 is different from grasping instrument 16 and is similar to that disclosed in prior application Ser. No. 08/847,191 incorporated herein by reference. Grasper 416 includes grasping members 450A and 450B forming a bullet shaped nose in the closed position with semi-circular recesses in distal ends of the grasping members 250A and 250B, respectively, cooperating to form a circular aperture 425 in the closed position as shown in FIG. 27b. The grasper 416 includes a selectively extendable, selectively retractable hollow needle 417 aligned with aperture 425 and movable between a retracted or withdrawn position wherein a tissue penetrating distal tip 421 of the needle is disposed proximally of and does not protrude through the aperture 425 and a fully extended position wherein the needle 417 extends through the aperture 425 such that the tip 421 is disposed distally of the grasping members 450A and 450B as shown in FIG. 27b, it being noted that FIG. 27a corresponds to a retracted position for the needle 417. The grasping members 450A and 450B are movable between an open position, depicted in FIG. 27a, and a closed position, depicted in FIG. 27b, via operation of a handle at a proximal end of the grasper 416 as disclosed above for grasping instrument 16 and as disclosed in application Ser. No. 08/847,191 incorporated herein by reference.

FIG. 27a illustrates use of ligating instrument 418 to form a ligature L in pedicle P of a pedunculated tissue structure T, i.e. a cyst, with the ligature loop 478 of the ligating instrument 418 contracted around the pedicle P to form the ligature L while the tissue body B is grasped by the grasping members 450A and 450B. Following formation of the ligature L and while the tissue body B remains grasped by the grasping members 450A and 450B, the needle 417 is moved via the handle from the retracted position to a less than fully extended position causing tip 421 of the needle to penetrate the body B of tissue structure T as shown in dotted lines in FIG. 27a, allowing cystic fluid to drain therefrom. It should be appreciated that a proximal end of the needle 417 can be connected to a source of suction or vacuum for aspiration of cystic fluid through the needle. It should also be appreciated that various fluids can be supplied or injected into the tissue structure T via the needle 417, such fluids being introduced though the needle from the proximal end thereof. FIG. 27a illustrates penetration of tissue body B prior to cutting connecting segment 482 proximally of the ligature L. It should be appreciated, however, that the tissue structure T can be penetrated with needle 417 subsequent to cutting the connecting segment 482 proximally of the ligature L depending on procedural use, the connecting segment 482 being cut with cutting edges of the grasping members 450A and 450B as previously described. The needle 417 can be moved to the fully extended position or to a less than fully extended position depending on the depth of penetration desired for the needle 417 in the tissue structure T. The prior application Ser. No. 08/847,191 discloses handle structure suitable for use at a proximal end of the grasper 416 to move the grasping members 450A and 450B between the open and closed positions and to extend and retract the needle 417.

Subsequent to penetration and drainage of the tissue body B, the needle 417 is retracted to withdraw tip 421 from the tissue structure T. The connecting segment 482 is cut proximally of the ligature L, if not cut prior to penetration and drainage of tissue body B, to sever or disconnect the ligature L from the remainder of the ligature supply. If desired, the tissue structure T is cut proximally of the ligature L, prior to or subsequent to cutting of segment 482. The tissue structure T can be cut with cutting edges of grasping members 450A and 450B in the manner previously described, and the portion or segment of tissue structure T that is cut is withdrawn from the patient's body.

FIG. 27b illustrates use of needle 417 to penetrate tissue structure T with the grasping members 450A and 450B in the closed position following release or disengagement of the tissue structure T from the grasping members 450A and 450B. As shown in FIG. 27b, the grasping members 450A and 450B are disengaged or released from the tissue body B and are moved to the fully closed position. The needle 417 is moved from the retracted position to the fully extended position, and the tip 421 is used to penetrate the tissue structure T at a desired penetration location. The instrument assembly 410 can be manipulated as needed to position the needle to penetrate the tissue structure T at the desired penetration location and angle. It should be appreciated that the needle 417 can be used to supply energy, such as electricity, laser, ultrasound and cryoenergy, to the anatomical tissue. Penetration of the anatomical tissue structure T can be visualized with a remote viewing device (not shown) disposed in barrel 412 as disclosed above for anatomical tissue ligating instrument assembly 10.

Figure 28:
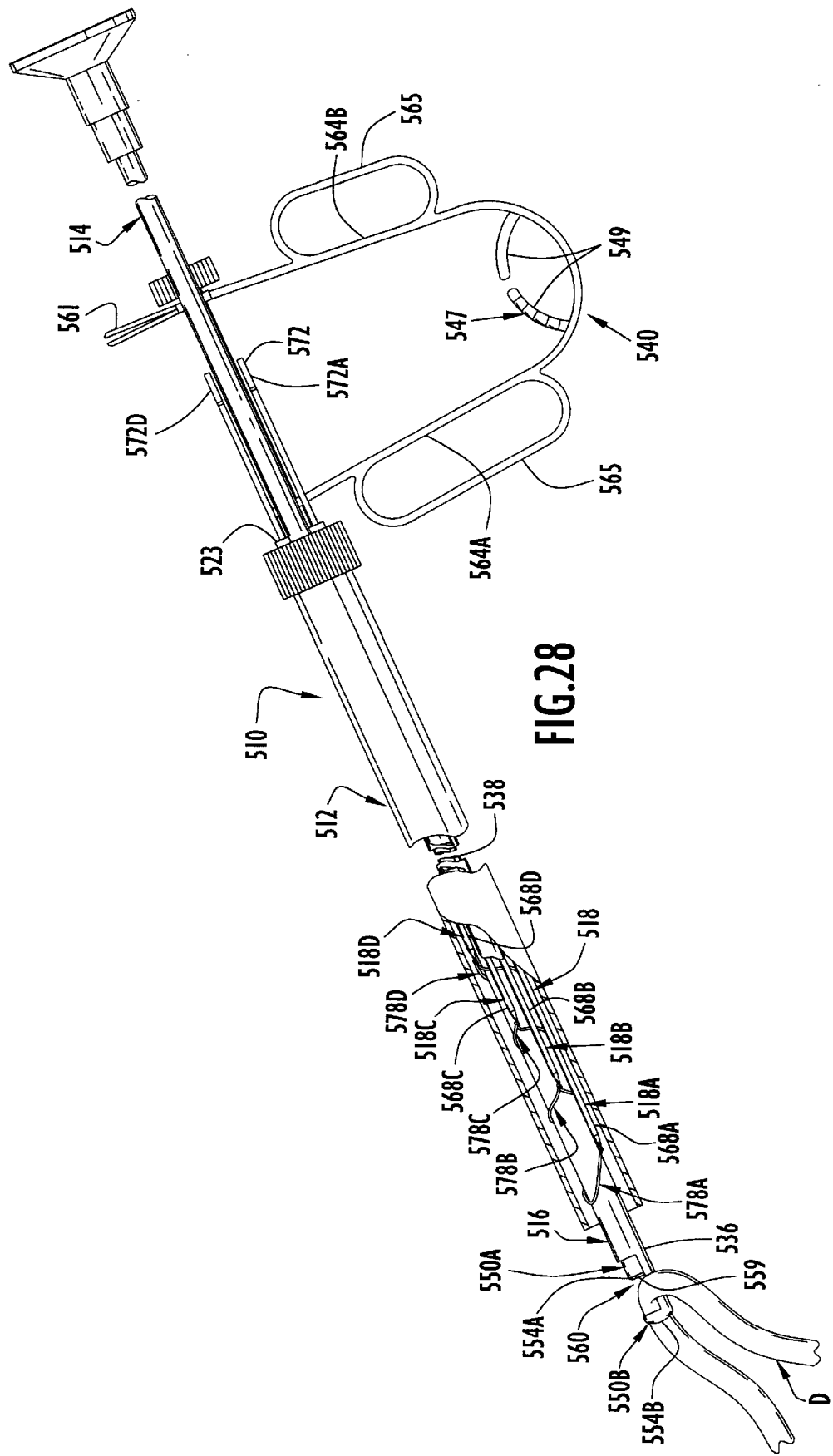
FIG. 28 is a broken side view, partly in section, of a fifth modified anatomical tissue ligation instrument assembly showing the grasping members of the grasper of the fifth modified anatomical tissue ligation instrument assembly in the open position receiving anatomical tubular structure therebetween.

A method of forming multiple or plural ligatures in the same anatomical tissue or in separate, distinct anatomical tissue utilizing an anatomical tissue ligation instrument assembly having a plurality of ligating devices is illustrated in FIGS. 28–31. The anatomical tissue ligation instrument assembly 510 illustrated in FIG. 28 includes a barrel 512 and a remote viewing device 514, a grasper 516 and a plurality of ligating devices 518 extending through barrel 512, the instrument assembly 510 including four ligating devices 518*a*, 518*b*, 518*c* and 518*d*. Barrel 512 is similar to barrel 12, and ligating devices 518*a*, 518*b*, 518*c* and 518*d* are similar to ligating device 18 with ligating devices 518*a*, 518*b*, 518*c* and 518*d* being of different lengths. The ligating devices 518*a*, 518*b*, 518*c* and 518*d* are arranged from longest to shortest around grasper 516 with the tubular members 568*a*, 568*b*, 568*c* and 568*d* thereof removably, slidably disposed in respective apertures in an annular flange 523 having a central hole through which the grasper 516 slidably passes, the tubular members 568*a*, 568*b*, 568*c* and 568*d* being frictionally held in the apertures. The proximal ends 572 of ligating devices 518*a*, 518*b*, 518*c* and 518*d*, respectively, are disposed proximally of flange 523 as shown in FIG. 28 for visible proximal ends 572*a* and 572*d* allowing the proximal ends 572 to be separated or broken away from the remainders of tubular members 568*a*, 568*b*, 568*c* and 568*d*, respectively, such that the ligature loops 578*a*, 578*b*, 578*c* and 578*d* can be contracted, respectively, as described above for ligating device 18. The ligating devices 518*a*, 518*b*, 518*c* and 518*d* are close to the grasper 516 and are disposed in the same passage or channel in barrel 512 as the grasper 516. However, it should be appreciated that the ligating devices 518*a*, 518*b*, 518*c* and 518*d* can be disposed in respective channels or passages of the barrel 512.

Figure 31:
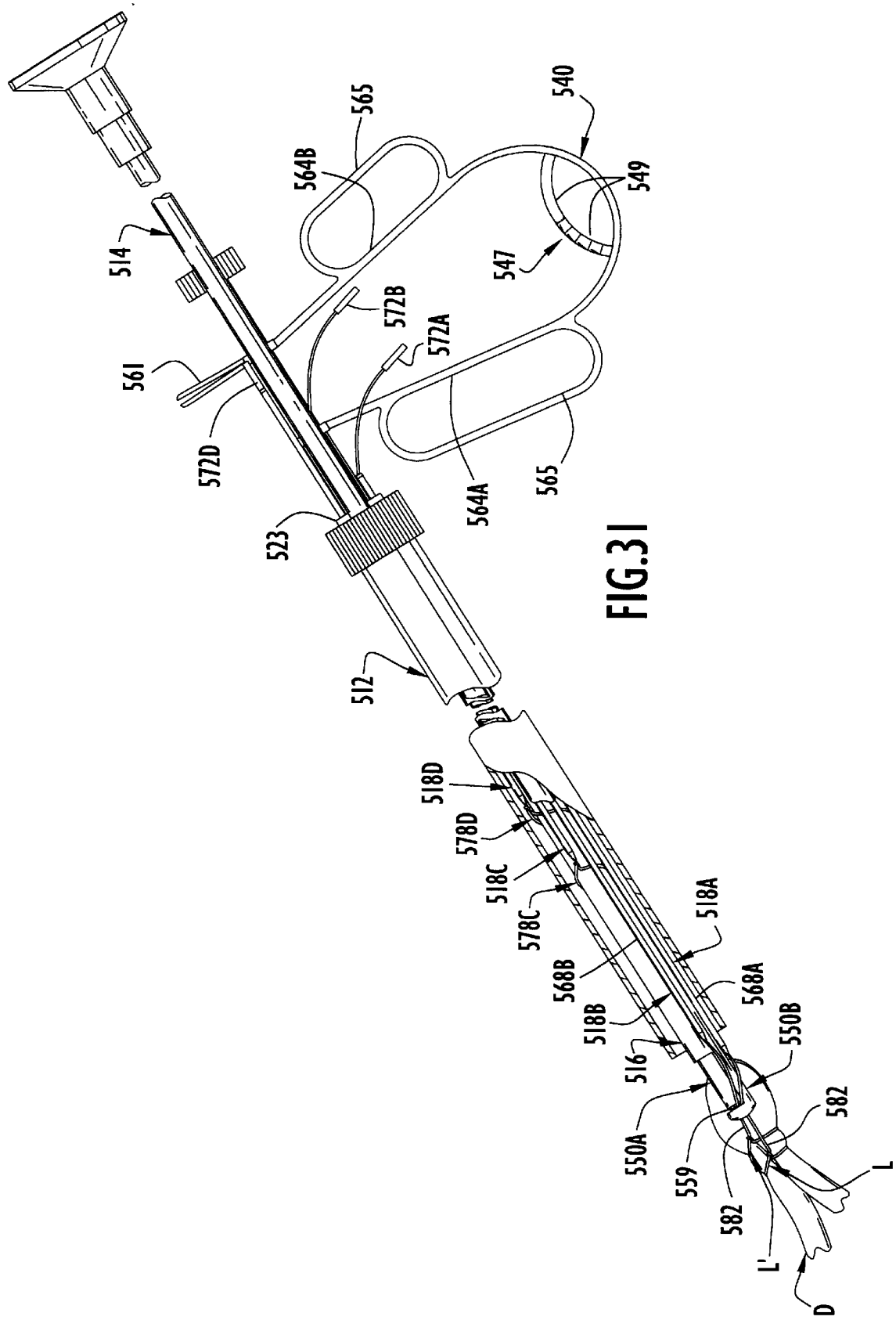
FIG. 31 is a broken side view, partly in section, depicting cutting of the ligature material of the first and second ligators proximally of the first and second ligatures, respectively.

Grasper 516 is similar to that disclosed in the prior application Ser. No. 08/847,191 incorporated herein by reference and includes outer member 536 connected to distal leg 564A of handle 540 and tubular inner member 538 connected to proximal leg 564B of handle 540. The handle 540 is similar to handle 40 except for the provision of a different locking mechanism 547. The locking mechanism 547 comprises a pair of curved locking arms or bars 549 carrying locking structure cooperatively engageable to lock the handle 540 in various incremental compressed positions as shown in FIG. 31. Outer member 536 carries or forms grasping member 550B having an inwardly angled distal tip 554B and a recess 560 disposed proximally of distal tip 554B. Inner member 538 terminates distally at grasping member 550A having a circumferential distal edge defining a distal tip 554A parallel to tip 554B. A proximal end of inner member 538 preferably extends proximally of handle 540 and carries a knob for rotating the inner member 538 relative to the outer member 536 and a valve for controlling fluid flow through the inner member 538. A connector 561, which can be a unipolar or bipolar electrical connector, is provided on handle 540 and is coupled with inner member 538 for transmitting electricity via the inner member 538 to grasping member 550A.

Handle 540 in the rest position positions the grasping members 550A and 550B in a closed or non-grasping position wherein the distal tip 554A is in contact with or close to the distal tip 554B such that the recess 560 of grasping member 550B is closed, occupied, blocked or filled by the grasping member 550A and cannot accommodate anatomical tissue therein. When the handle 540 is spread via finger rings 565, the outer member 536 is moved longitudinally, distally relative to the inner member 538 and/or the inner member 538 is moved longitudinally, proximally relative to the outer member 536 causing the grasping members 550A and 550B to be moved to the open or grasping position shown in FIG. 28 wherein distal tips 554A and 554B are spaced further from one another to open or present recess 560 to receive anatomical tissue therein. Release of the spreading force on handle 540 causes the handle 540 to return automatically to the rest position with return of the grasping members 550A and 550B to the closed position. The distal tip 554A carries or is formed as a cutting edge 559 to cut anatomical tissue disposed in recess 560 when the grasping members are moved from the open position toward the closed position.

Figure 29:
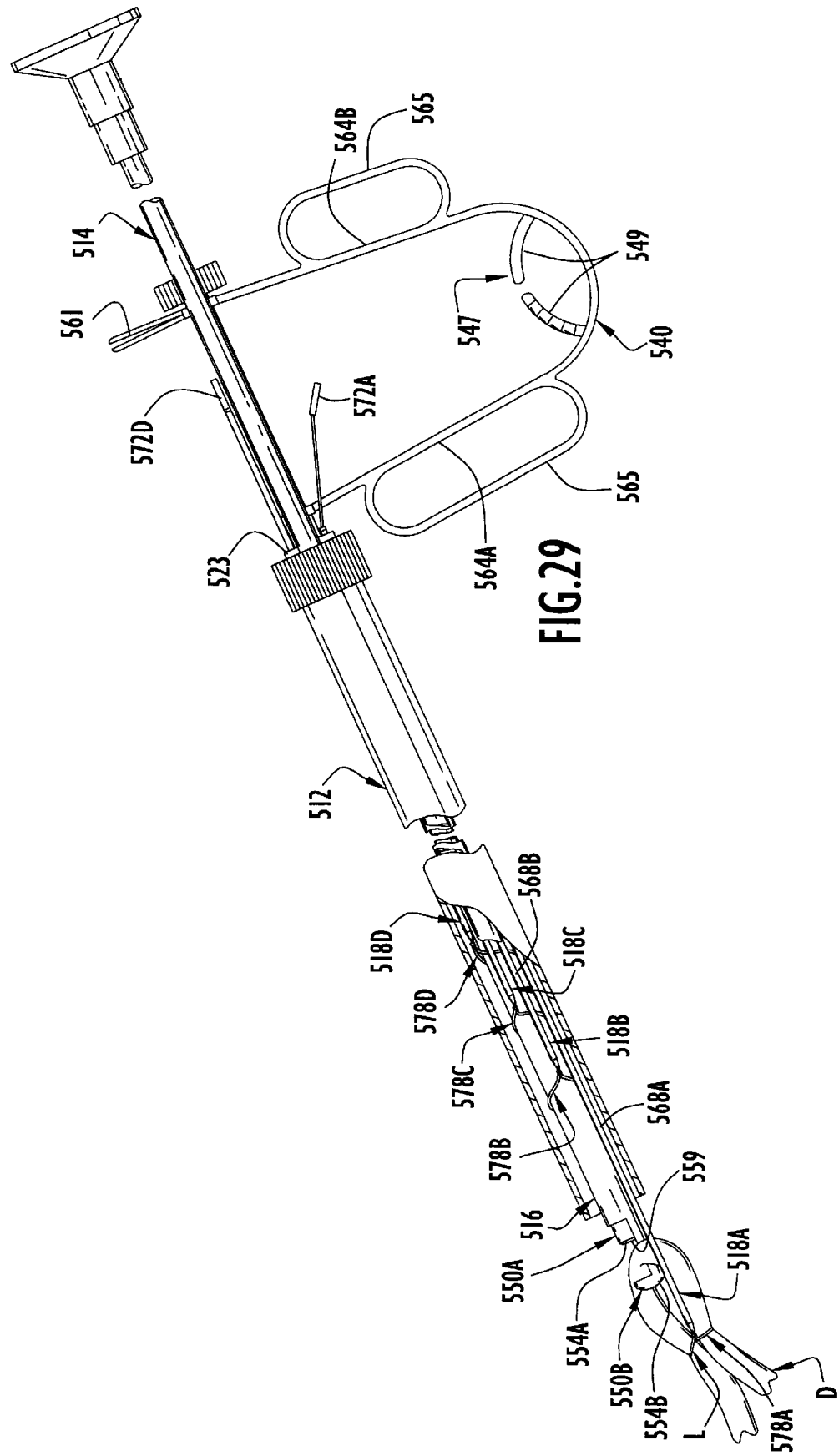
FIG. 29 is a broken side view, partly in section, illustrating formation of a first ligature in the grasped anatomical tubular structure with a contractible ligature loop of a first ligator carried by the grasper of the fifth modified anatomical tissue ligation instrument assembly.

FIG. 28 illustrates a distal end of instrument assembly 510 introduced at an operative site with the ligature loops 478*a*, 478*b*, 478*c* and 478*d* disposed around the grasper 516 such that the grasper passes through the ligature loops. The ligature loops 478*a*, 478*b*, 478*c* and 478*d* are disposed in barrel 512 when the distal end of the instrument assembly 510 is introduced at the operative site; however, it should be appreciated that one or more of the ligature loops can be disposed externally of barrel 512 when the distal end of the instrument assembly is introduced at the operative site. The grasping members 550A and 550B are moved to the open position via spreading operation of handle 540 to receive anatomical duct D in the recess 560 with the duct D extending transverse to a longitudinal axis of the grasper 516, the distal tip 554B acting as a hook or finger for picking up or grabbing the duct D and drawing it into a loop formation. Once the duct D has been drawn into a loop formation, the longest ligating device 518*a* is advanced distally relative to the rest of the instrument assembly to position the ligature loop 578*a* around the loop formation. The ligating device 518*a* is distally advanced along the grasper 516 by moving the tubular member 568*a* thereof distally within the flange 523 and the barrel 512 causing the ligature loop 578*a* to move off of the grasper 516 and onto the loop foundation of duct D as shown in FIG. 29. Once the ligature loop 578*a* has been positioned over or around the loop formation, the proximal end 572*a* is broken off from the remainder of tubular member 568*a*, which remains frictionally held in flange 523. The proximal end 572*a* is drawn proximally to contract ligature loop 578*a* around the loop formation to form a ligature L as shown in FIG. 29.

Figure 30:
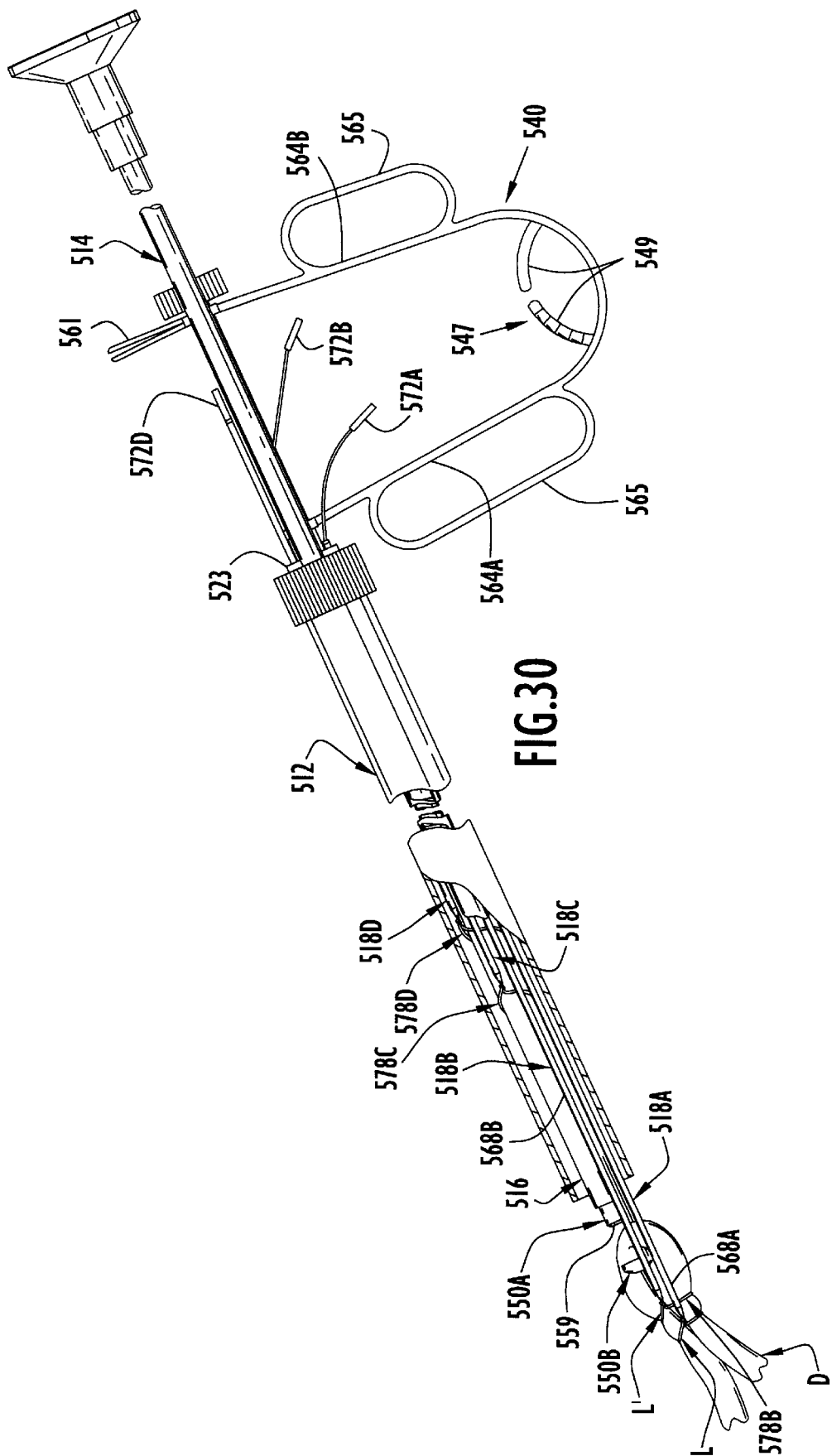
FIG. 30 is a broken side view, partly in section, illustrating formation of a second ligature in the anatomical tubular structure with a contractible ligature loop of a second ligator carried by the grasper of the fifth modified anatomical tissue ligation instrument assembly.

As shown in FIG. 30, the next longest ligating device 518*b* is advanced distally relative to the rest of the instrument assembly 510 to position the ligature loop 578*b* around the loop formation. The proximal end 572*b* of tubular member 568*b* is separated from the remainder of the tubular member 568*b* and is drawn proximally in the manner described for ligating device 518*a* to contract the ligature loop 578*b* around the loop formation of duct D to form another ligature L' while the loop formation remains held by the grasping members. Ligature L' is formed in the loop formation proximally of ligature L; however, the ligature L' can be formed at any other desired location on duct D. Following formation of the ligature L' and any additional ligatures to be formed in duct D with ligating devices 518*c* and/or 518*d*, the grasping members 550A and 550B are used to cut the segments 582 of ligature material extending from the ligatures. FIG. 31 shows grasping members 550A and 550B disengaged from the duct D and the segments 582*a* and 582*b* of ligature material extending proximally from ligatures L and L', respectively, positioned in the recess 560.

The grasping members 550A and 550B are moved to a more tightly closed position via squeezing operation of handle 540 to cut the segments 582a and 582b with the cutting edge 559 to separate the ligatures L and L' from the ligating devices 518a and 518b, respectively. The ligating devices 518a and 518b can then be withdrawn from flange 523 by slidably withdrawing the ligating devices 518a and 518b from the corresponding apertures in flange 523 for removal from the instrument assembly 510.

Figure 32:
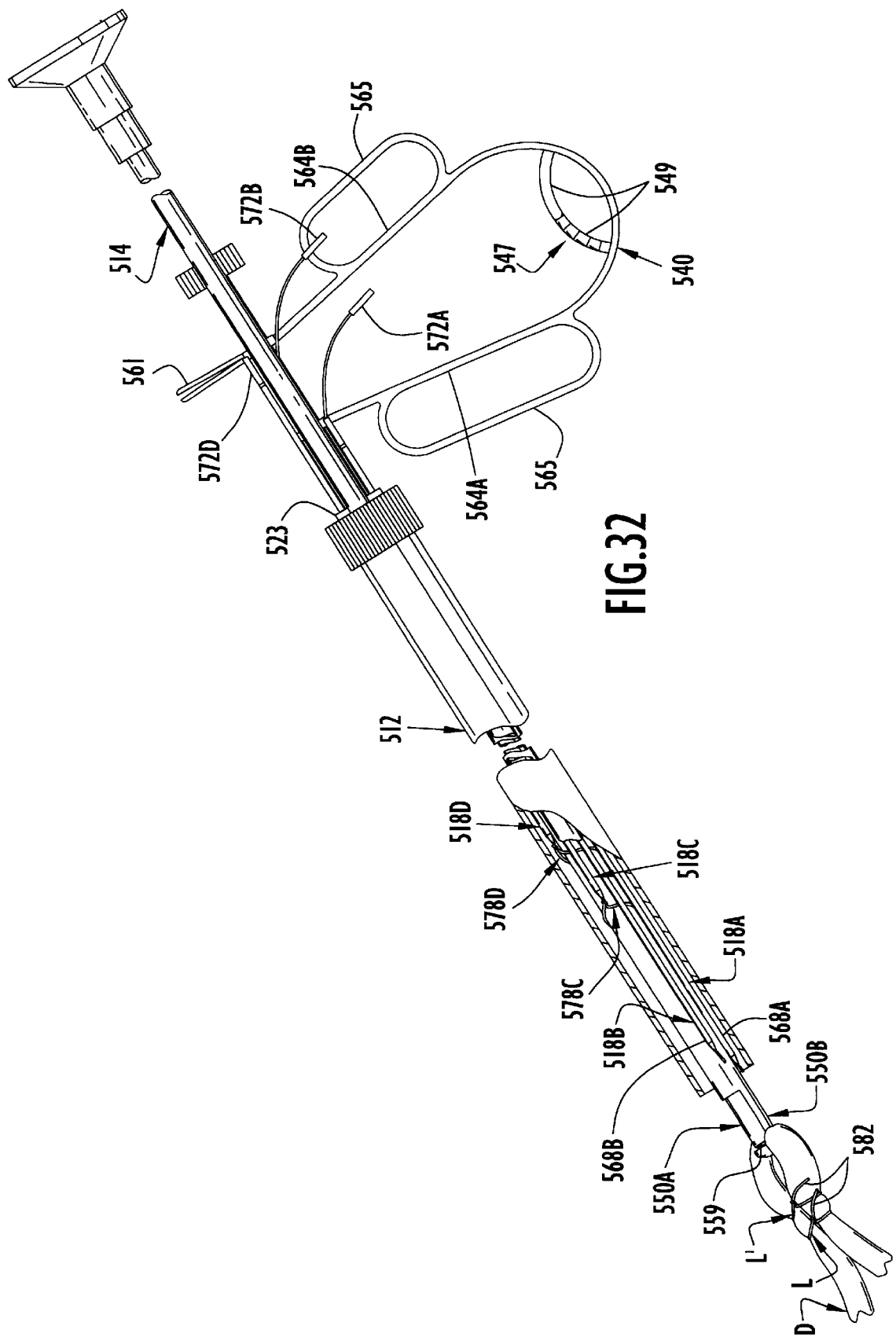
FIG. 32 is a broken side view, partly in section, illustrating cutting of a segment of the anatomical tubular structure proximally of the first and second ligatures.

If desired, the ligating devices 518a and 518b can remain in place and not be withdrawn from the instrument assembly. For example, FIG. 32 illustrates the ligating devices 518a and 518b moved proximally relative to the rest of the instrument assembly to be retracted or disposed within the barrel 512. If desired, a segment of the loop formation of duct D can be cut proximally of the ligatures L and L', or between the ligatures L and L'. FIG. 32 illustrates grasping members 550A and 550B grasping a segment of the loop formation of duct D proximally of the ligature L' with the handle 540 squeezed or compressed to cut the segment of the loop formation with the cutting edge 559. The cut segment is captured in the cutting members and is withdrawn from the instrument assembly 510 via suction applied through the inner member 538 for retrieval of the cut segment external of the patient's body. If indicated, the grasping members 550A and 550B can be used for electric cautery or coagulation.

It should be appreciated that the instrument assembly 510 can remain at the operative site to form additional ligatures with ligating devices 518c and 518d. The instrument assembly can include any number of ligating devices 518 in accordance with the number of ligatures to be formed. Although ligatures L and L' are both formed in the duct D, it should be appreciated that ligatures can be formed with the instrument assembly 510 in the same anatomical tissue at the same or different locations or in separate or distinct anatomical tissue. It should be further appreciated that the grasping members 550A and 550B are particularly useful for grasping or holding a needle, such as a suture needle, therebetween as accomplished with increased grasping force or pressure obtained through squeezing operation of the handle.

The endoscopes can be movably or slidably disposed in the barrels to permit optimal positioning during the procedure; however, the endoscopes can be non-separable from the barrels and can be formed as non-removable and/or non-movable parts of the barrels, such as being formed integrally, unitarily with the barrels. The barrels can be designed to transmit an image of the operative site for remote viewing thusly eliminating the need for a separate endoscope. The endoscopes themselves can be designed to define channels for receiving the grasping instruments and/or the ligating instruments as well as other instruments without the need for separate barrels. The endoscopes can be designed or selected to transmit light for illumination of the operative site as well as to transmit an image of the operative site for remote viewing. The endoscopes can be rigid or flexible or bendable, and the endoscopes can be partly rigid and partly flexible or partly bendable. The endoscopes can be designed or provided with various accessories or adjustment features including focus, zoom and magnification adjustments or features and a CCD (charge coupled device). The endoscopes can be offset, branched or bifurcated and can include pivotable or hinged segments. The endoscopes can be designed in many various ways and can include fiber optic rod lens systems, various multiple lens systems or digital endoscope systems.

The grasping instruments can be designed in many various ways with a single grasping member or multiple grasping members. The grasping members can be pivotable, rotatable or longitudinally movable for movement between open and closed positions; and, where multiple grasping members are provided, some of the grasping members can be fixed or immovable. The grasping members can be designed to be disposed in the open position when the grasping instrument or handle therefor is in the rest position, or the grasping members can be designed to be disposed in the closed position when the grasping instrument or handle therefor is in the rest position. For example, the grasping members can be biased to the open position and be unconstrained to remain in the open position in the rest position, or the grasping members can be constrained in the rest position to be disposed in the closed position. The grasping members do not have to be biased to the open position. For example, the grasping members can be mechanically moved to the open and closed positions, and the grasping members can be biased to the closed position. The inner and outer members of the grasping instruments can both move relative to one another to move the grasping members between the open and closed positions, or one of the inner and outer members can move relative to the other to move the grasping members between the open and closed positions.

The grasping surfaces of the grasping members can be provided with serrations or teeth or other structure or formations to facilitate gripping the anatomical tissue and for other functions such as holding a needle. The grasping members can be used to transmit energy and/or can function as clip appliers as well as needle holders. The grasping instruments can include various handle structure including pivotable members, pistol grips and triggered members of spring or flexible materials as well as rigid materials. The inner members of the grasping instruments can have various structural configurations including tubes, plates and wires, for example. The grasping instruments can be made integrally, unitarily with the ligating instruments, and a single handle can be provided to operate the grasping instrument and the ligating instrument. Various additional instruments, such as needles, can be introduced through the grasping instruments, and such additional instruments can be made integral with the grasping instruments.

Various grasping members, instruments or graspers suitable for use in the methods according to the present invention are disclosed in prior applications Ser. No. 08/847,252 filed May 1, 1997 and entitled Surgical Instrument with Rotatably Mounted Offset End Effector and Method of Using the Same, Ser. No. 08/847,189 filed May 1, 1997 and entitled Surgical Instrument with Multiple Rotatably Mounted Offset End Effectors and Method of Using the Same, Ser. No. 08/847,253 filed May 1, 1997 and entitled Suturing Instrument with Rotatably Mounted Offset Needle Holder and Method of Using the Same, and Ser. No. 08/847,254 filed May 1, 1997 and entitled Suturing Instrument with Multiple Rotatably Mounted Offset Needle Holders and Method of Using the Same, the disclosures of all of the latter applications being incorporated herein by reference.

The cutting members can be designed in many various ways to cut anatomical tissue. The cutting members can include structure for enclosing or capturing cut anatomical tissue, and such structure can have sizes and configurations in accordance with the types of tissue to be enclosed or captured. The cutting members can be used to cut or sever the ligature material and/or the anatomical tissue. Cutting members for cutting the ligature material and/or the anatomical tissue as well as for capturing the anatomical tissue can be provided as one or more separate cutting instruments, and such cutting members can be provided on the ligating instruments.

The ligating instruments, ligating devices or ligators can include Endoloop™-type ligating devices which can be provided with various handles operable to contract the ligature loops. The ligating instruments can include the various devices, adapters and instruments disclosed in prior application Ser. No. 930,320, filed Aug. 17, 1992 and now U.S. Pat. No. 5,334,199, Ser. No. 195,491, filed Feb. 14, 1994 and now U.S. Pat. No. 5,486,186, Ser. No. 452,756, filed May 30, 1995 and now U.S. Pat. No. 5,571,120, Ser. No. 531,153, filed Sep. 15, 1995, Ser. No. 08/533,504 filed Sep. 25, 1995 and Ser. No. 08/694,385, filed Aug. 8, 1996, all incorporated herein by reference. The ligature supplies can include a single ligature loop or a plurality of ligature loops; and, where the ligature supply includes a plurality of ligature loops, the ligature loops can be interconnected or not connected to one another. The ligature supplies can include ligature loops sufficient in number to complete a ligation procedure without withdrawing the ligating instruments or the instrument assemblies from the operative sites. A plurality of ligating instruments, ligating devices or ligators can be used in a single anatomical tissue ligation. The ligating instruments can have various handles operable with one hand to contract the one or more ligature loops and to perform other functions depending upon the design of the ligating instruments, such as the functions of deploying ligature loops of the ligating instruments in sequence and cutting the lengths of ligature material proximally of ligatures formed with the ligature loops. Various handle structures for the ligating instruments are disclosed in the prior patents and applications incorporated herein by reference. The ligature material can be absorbable, non-absorbable and/or stretchable in accordance with the procedure to be performed. The ligature loops can include various knotting elements including preformed knots formed by tying the ligature material as well as other knotting elements such as those described in the patents and applications incorporated herein by reference.

The grasping instruments and the ligating instruments can be arranged in many various ways within the passage defining members, such as side by side and concentrically. The instrument assemblies can be utilized in single port and multiple port endoscopic procedures as well as non-endoscopic and mini-lap procedures. The endoscopes, the grasping instruments and/or the ligating instruments can be designed to allow fluid flow therethrough and/or to allow additional instruments to be introduced therethrough, such as needles for penetrating anatomical tissue and/or administering medicaments such as anesthetic agents. The barrels and/or the endoscopes can be provided with additional channels for supplying medicaments and/or irrigating fluids, for aspirating fluids and/or for introducing additional instruments.

The endoscopes, the grasping instruments and/or the ligating instruments can be withdrawn from the patients' bodies separately, individually or simultaneously and together as one or more units. The endoscopes, the grasping instruments and the ligating instruments can all be longitudinally movable relative to the barrels. The grasping instruments and/or the ligating instruments can be longitudinally movable relative to the endoscopes and/or relative to one another. Instrument assemblies suitable for use in the methods of the present invention are disclosed in prior application Ser. No. 08/847,191 incorporated herein by reference.

Various types of anatomical tissue can be ligated in accordance with the methods of the present invention, such tissue including non-tubular and tubular tissue or structure such as polyps, cysts, fibroids, growths such as tumors, blood vessels, ducts, appendages and organs, for example. The ligated anatomical tissue can be cut proximally of the ligature to create a stump of tissue at the ligature. Where the ligated tissue is tubular, the tubular tissue can be severed proximally of the ligature to create a pair of free ends. A single ligature or multiple ligatures can be formed in the anatomical tissue. Where multiple ligatures are formed in the anatomical tissue, the multiple ligatures can be formed with the same instrument assembly and without withdrawing the instrument assembly from the operative site. More than one anatomical tissue mass, portion or structure can be ligated with a single instrument assembly, and the single instrument assembly can be used to form ligatures in plural tissue masses, portions or structures, respectively, without withdrawing the instrument assembly from the operative site. The same instrument assembly used to ligate the anatomical tissue can be used to treat the anatomical tissue with energy, such as electricity, laser, ultrasound and cryoenergy. The instrument assembly used to ligate the anatomical tissue can be provided or combined with a needle for penetrating or puncturing the anatomical tissue. For example, a cyst can be tied off with a ligature at its base or stem and thereafter the cyst can be punctured with a needle of the instrument assembly to drain cystic fluid therefor. The needle of the instrument assembly can be used to treat anatomical tissue via fluid injection.

With the present invention, a single instrument assembly is used to grasp anatomical tissue, to position a contractible ligature loop around the grasped anatomical tissue and to contract the ligature loop around the anatomical tissue to form a ligature. In addition, the same instrument assembly can be used to cut the anatomical tissue and/or the ligature material proximally of the ligature. The ligature loop is placed around the anatomical tissue and contracted to form the ligature while the anatomical tissue remains held or grasped by the grasper of the instrument assembly. The ligature material can be cut or severed proximally of the ligature prior to or subsequent to cutting of the anatomical tissue proximally of the ligature. Depending on the procedure being performed, the anatomical tissue may not have to be cut proximally of the ligature.

Inasmuch as the present invention is subject to various modifications and changes in detail, the above description of the preferred embodiments is intended to be exemplary only and not limiting.

What is claimed is:

1. A method of anatomical tissue ligation comprising the steps of introducing a distal end of an anatomical tissue ligation instrument assembly at an internal operative site in a patient's body with a proximal end of the anatomical tissue ligation instrument assembly disposed external of the patient's body; wherein said step of introducing includes introducing the distal end of the anatomical tissue ligation instrument assembly at the internal operative site through a small size port providing communication with the internal operative site from external of the patient's body and further including the step of visualizing the internal operative site, from external of the patient's body, with an endoscope;

grasping anatomical tissue at the internal operative site with a grasping member of the anatomical tissue ligation instrument assembly disposed at the distal end;

positioning a contractible, closed ligature loop of filamentous ligature material of the anatomical tissue ligation instrument assembly around the anatomical tissue while the anatomical tissue remains grasped by the grasping member;

contracting the ligature loop around the anatomical tissue, from the proximal end of the anatomical tissue ligation instrument assembly, to form a ligature while the anatomical tissue remains grasped by the grasping member;

releasing the anatomical tissue from the grasping member; and cutting the ligature material proximally of the ligature with a cutting blade of the anatomical tissue ligation instrument assembly to sever the ligature from the remainder of the ligature material.

2. A method of anatomical tissue ligation as recited in claim 1 wherein said step of introducing includes introducing the distal end of the anatomical tissue ligation instrument assembly at the internal operative site with the ligature loop disposed around the grasping member.

3. A method of anatomical tissue ligation as recited in claim 1 wherein said step of grasping includes grasping the anatomical tissue between a pair of grasping members disposed at the distal end of the anatomical tissue ligation instrument assembly.

4. A method of anatomical tissue ligation as recited in claim 3 wherein said step of grasping includes moving the grasping members between an open position to receive the anatomical tissue between the grasping members and a closed position to grasp the anatomical tissue between the grasping members.

5. A method of anatomical tissue ligation as recited in claim 4 wherein said step of moving the grasping members includes pivotally moving the grasping members between the open and closed positions.

6. A method of anatomical tissue ligation as recited in claim 1 wherein said step of positioning includes moving the ligature loop longitudinally, distally relative to the grasping member to place the ligature loop around the anatomical tissue.

7. A method of anatomical tissue ligation as recited in claim 1 wherein the ligature loop includes a loop segment of the length of filamentous ligature material and a knotting element slidable along the length of filamentous ligature material and said step of contracting includes moving the knotting element along the length of filamentous ligature material in the direction of the loop segment to contract the loop segment around the anatomical tissue to form the ligature.

8. A method of anatomical tissue ligation comprising the steps of introducing a distal end of an anatomical tissue ligation instrument assembly at an internal operative site in a patient's body;

grasping a pedunculated anatomical structure at the internal operative site between a pair of grasping members of the anatomical tissue ligation instrument assembly disposed at the distal end;

positioning a contractible ligature loop of the anatomical tissue ligation instrument assembly disposed at the distal end around a pedicle of the pedunculated anatomical structure while the pedunculated anatomical structure remains grasped by the grasping members;

contracting the ligature loop around the pedicle to form a ligature;

severing a portion of the pedunculated anatomical structure proximally of the ligature with the distal end of the anatomical tissue ligation instrument assembly to create a stump of anatomical tissue at the ligature supplying energy to the stump; and removing the severed portion from the patient's body.

9. A method of anatomical tissue ligation as recited in claim 8 wherein the pedunculated anatomical structure includes a tissue body connected to the pedicle and said step of grasping includes grasping the tissue body.

10. A method of anatomical tissue ligation as recited in claim 9 wherein said step of severing includes severing the tissue body from the pedicle.

11. A method of anatomical tissue ligation as recited in claim 10 wherein said step of severing includes severing the pedunculated anatomical structure with the grasping members.

12. A method of anatomical tissue ligation as recited in claim 11 wherein said step of severing includes receiving the pedunculated anatomical structure between cutting members of the grasping members disposed in a non-cutting position and moving the cutting members from the non-cutting position to a cutting position to sever the pedunculated anatomical structure with the cutting members.

13. A method of anatomical tissue ligation as recited in claim 12 wherein said step of severing includes capturing the severed portion between the grasping members.

14. A method of anatomical tissue ligation as recited in claim 13 wherein said step of removing includes withdrawing the grasping members from the patient's body while the rest of the distal end of the anatomical tissue ligation instrument assembly remains at the operative site.

15. A method of anatomical tissue ligation as recited in claim 13 wherein said step of removing includes withdrawing the distal end of the anatomical tissue ligation instrument assembly from the patient's body.

16. A method of ligating an anatomical tubular structure at an internal operative site in a patient's body comprising the steps of introducing a distal end of an anatomical tissue ligation instrument assembly at the operative site with a proximal end of the anatomical tissue ligation instrument assembly disposed external of the patient's body; providing the anatomical tissue instrument assembly with an endoscope extending through a barrel and further including, subsequent to said step of introducing, the step of visualizing the operative site with the endoscope from external of the patient's body;

grasping an anatomical tubular structure at the internal operative site with a grasping member of the anatomical tissue ligation instrument assembly disposed at the distal end;

moving the grasping member proximally to bend the anatomical tubular structure;

positioning the bend through a contractible, closed ligature loop of a ligature supply of the anatomical tissue ligation instrument assembly comprising a continuous length of filamentous ligature material forming the ligature loop externally of the distal end; and contracting the ligature loop around the bend, from external of the patient's body, to form a ligature in the anatomical tubular structure.

17. A method of ligating an anatomical tubular structure as recited in claim 16 wherein said step of introducing includes introducing the distal end of the anatomical tissue ligation instrument assembly at the operative site with the grasping member extending through the ligature loop and said step of positioning includes moving the ligature loop distally off of the grasping member and around the bend while the anatomical tubular structure is grasped by the grasping member.

18. A method of ligating an anatomical tubular structure as recited in claim 16 and further including, subsequent to said step of contracting, the step of severing the bend proximally of the ligature to form two free ends of the anatomical tubular structure extending proximally from the ligature.

19. A method of ligating an anatomical tubular structure as recited in claim 18 wherein said step of severing includes severing a segment of the bend from the remainder thereof and further including the step of removing the segment from the patient's body.

20. A method of ligating an anatomical tubular structure as recited in claim 18 and further including the step of cauterizing the free ends of the anatomical tubular structure.

21. A method of ligating anatomical tissue at an internal operative site in a patient's body comprising the steps of providing an anatomical tissue ligation instrument assembly including a barrel having a distal end and a proximal end, a grasper carried by said barrel and having a grasping member disposed externally of the distal end of the barrel and a ligator carried by said barrel and having an elongate member extending through the barrel and a contractible ligature loop coupled to the elongate member and disposed externally of a distal end of the elongate member and the distal end of the barrel;

introducing the distal end of the barrel at the internal operative site to position the grasping member and the ligature loop at the internal operative site; wherein said step of providing includes providing the anatomical tissue instrument assembly with an endoscope extending through the barrel and further including, subsequent to said step of introducing, the step of visualizing the operative site with the endoscope from external of the patient's body;

grasping anatomical tissue with the grasping member externally of the distal end of the barrel;

positioning the ligature loop around the anatomical tissue grasped by the grasping member externally of the distal end of the barrel;

contracting the ligature loop around the anatomical tissue to form a ligature;

releasing the ligature loop from the elongate member; and withdrawing the instrument assembly from the operative site leaving the ligature in the patient's body.

22. A method of ligating anatomical tissue as recited in claim 21 wherein said step of introducing includes introducing the distal end of the barrel at the internal operative site through a small size port extending through an anatomical wall and providing communication with the operative site from external of the patient's body.

23. A method of ligating anatomical tissue as recited in claim 22 and further including the step of transmitting light through the barrel to illuminate the operative site.

24. A method of ligating anatomical tissue as recited in claim 21 wherein said step of introducing includes introducing the distal end of the barrel at the operative site with the ligature loop disposed externally around the grasper.

25. A method of ligating anatomical tissue as recited in claim 21 wherein said step of providing includes providing the ligator with a ligature supply including a length of filamentous ligature material coupled with the elongate member and extending distally from the barrel to terminate at the ligature loop externally of the distal end of the barrel and said step of releasing includes cutting the length of ligature material proximally of the ligature to separate the ligature from the remainder of the ligature supply.

26. A method of ligating anatomical tissue as recited in claim 25 wherein said step of cutting includes cutting the ligature material with the grasping members.

\* \* \* \* \*